(12) United States Patent
Kao et al.

(10) Patent No.: US 8,066,981 B2
(45) Date of Patent: Nov. 29, 2011

(54) COMPOSITIONS AND METHODS RELATED TO TOLL-LIKE RECEPTOR-3

(75) Inventors: Cheng C. Kao, College Station, TX (US); Ranjith Kumar Tharachaparamba, Bloomington, IN (US)

(73) Assignee: The Texas A & M University System, College Station, TX (US)

( * ) Notice: Subject to any disclaimer, the term of this patent is extended or adjusted under 35 U.S.C. 154(b) by 313 days.

(21) Appl. No.: 11/985,251

(22) Filed: Nov. 14, 2007

(65) Prior Publication Data

US 2009/0142300 A1    Jun. 4, 2009

(51) Int. Cl.
*C07K 14/435* (2006.01)
*A61K 38/14* (2006.01)
*A61K 38/21* (2006.01)
*C12N 5/00* (2006.01)

(52) U.S. Cl. ...... 424/85.5; 424/85.4; 530/350; 530/395; 514/12.2; 514/29; 435/69.5; 435/320.1; 435/325; 435/375

(58) Field of Classification Search .................. None
See application file for complete search history.

(56) References Cited

U.S. PATENT DOCUMENTS

| | | | | |
|---|---|---|---|---|
| 5,225,539 | A | 7/1993 | Winter | 530/387.3 |
| 5,698,155 | A | 12/1997 | Grosswald et al. | 264/402 |
| 2003/0022302 | A1 | 1/2003 | Lewis et al. | 435/69.1 |
| 2003/0032090 | A1 | 2/2003 | Hardiman et al. | 435/69.1 |
| 2004/0162413 | A1 | 8/2004 | Watkins et al. | 435/6 |

FOREIGN PATENT DOCUMENTS

| | | | |
|---|---|---|---|
| WO | WO2006/060513 | * | 6/2006 |
| WO | WO 2006/111946 | | 10/2006 |

OTHER PUBLICATIONS

Sun et al, The Journal of Biological Chemistry, Apr. 21, 2006, vol. 281, No. 16, pp. 11144-11151.*
Choe et al, Science, Jul. 22, 2005, vol. 309, pp. 581-585.*
Bell et al., "Leucine-rich repeats and pathogen recognition in Toll-like receptors," *Trends Immunol.*, 24: 528-533 (2003).
Bell et al., "The Molecular Structure of the Toll-Like Receptor 3 Ligand-Binding Domain," *Proc Natl Acad Sci USA*, 102(31): 10976-10980 (2005).
Bell et al., "The DsRNA Binding Site of Human Toll-Like Receptor 3," *Proc Natl Acad Sci USA*, 103(23): 8792-8797 (2006).
Choe et al., "Crystal structure of human toll-like receptor 3 (TLR3) ectodomain," *Science*, 309: 581-585 (2005).
Funami et al., "Cytoplastic 'linker region' in Toll-like receptor 3 controls receptor localization and signaling," *Int Immunol.*, 16: 1143-1154 (2004).
Griffin et al., "Specific covalent labeling of recombinant protein molecules inside live cells," *Science*, 281: 269-272 (1998).
Kim et al., "Natural motifs that determine specificity between a viral replicase and its promoter," *Nat Struct Biol.*, 7: 415-423 (2000).
Ranjith-Kumar et al., "Biochemical and functional analyses of the human toll-like receptor 3 ectodomain," *J.B.C.*, 282: 7668 (2007).
Sechi et al., "Modification of cysteine residues by alkylation. A tool in peptide mapping and protein identification," *Anal. Chem.*, 70: 5150-5158 (1998).
Siegel et al., "Sequence-Specific Recognition of a Subgenomic RNA promoter by a Viral RNA Polymerase," *Proc Natl Acad Sci USA*, 94(21): 11238-11243 (1997).
Sun et al., "Structural and functional analyses of the human toll-like receptor-3: role of glycosylation," *J Biol Chem*, 281: 11144-11151 (2006).

* cited by examiner

*Primary Examiner* — Bridget E Bunner
*Assistant Examiner* — Fozia Hamud
(74) *Attorney, Agent, or Firm* — Medlen & Carroll, LLP

(57) ABSTRACT

The invention relates to compositions and methods related to Toll-like receptor (TLR) polypeptides. In some embodiments, the invention relates to managing TLR3 related diseases. In further embodiments, the invention relates to methods of preventing and treating inflammation. In some embodiments, the invention relates to antagonists of TLR3, to amino acid sequences that act as dominant negative molecules, and to nucleic acid sequences that encode said amino acid sequences. In additional embodiments, the invention relates to the manipulation of biological materials to evaluate TLR3 activity.

5 Claims, 28 Drawing Sheets
(6 of 28 Drawing Sheet(s) Filed in Color)

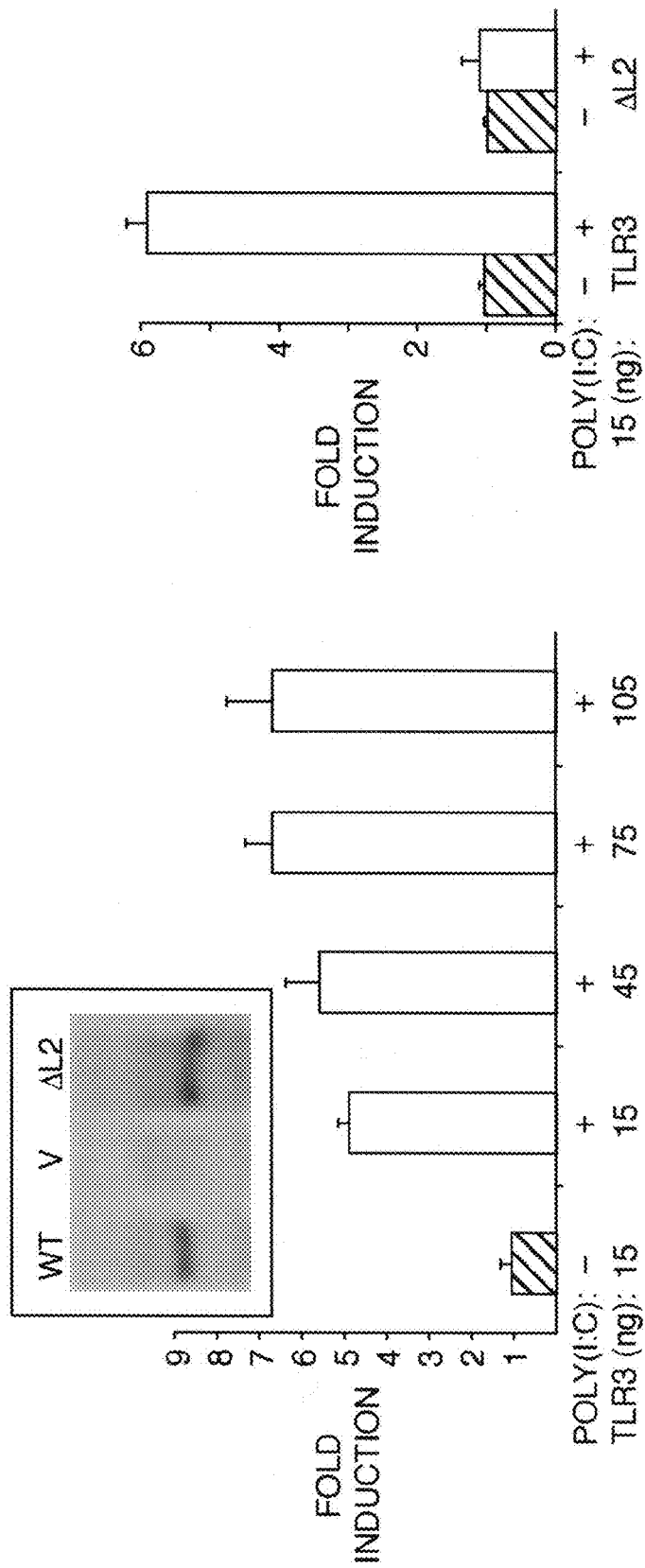

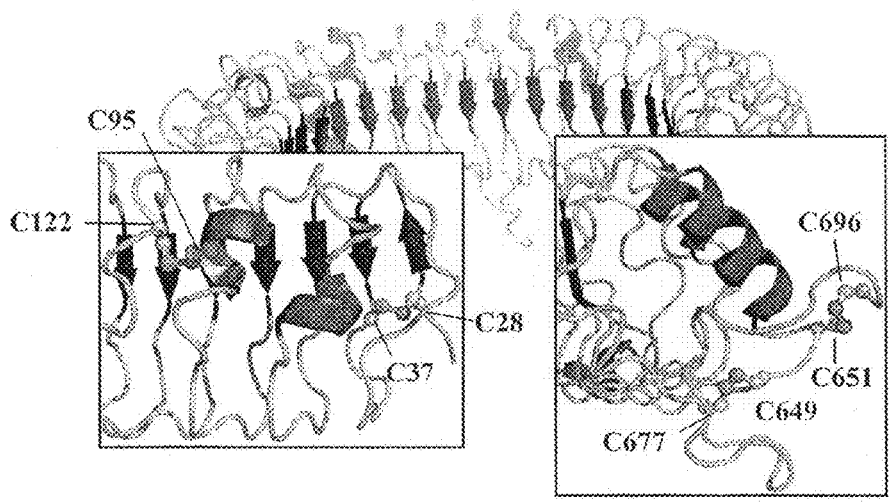

FIG. 2A

```
         28    37 95              122
Homo    CTVSHEVADC  CQKLPMLKVLNLQHNELSQLSDKTFAFC
Pans    CTVTHEVADC  CQKLPMLKVLNLQHNELSQLSDKTFAFC
Bos     CTVRHEVADC  CQSLPWLEILNLQHNEISQLSDKTFIFC
Rattus  CTVRYNVADC  CQILPLLKVLNLQHNELSQISDQTFAFC
Mus     CTVRYNVADC  CQILPLLKVLNLQHNELSQISDQTFVFC
Fugu    CVVQGSSADC  CETLPRLQTLDVAHNQVLALREEDLSRC
Tetradon CRVQGDSADC CETLPRLRTLNVAHNQLLTLREEDLNPC 649 651      677      696
Homo    CTCESIAWFVNWINETH TNIPELSSHYLCNTPPHYHGFPVRLFDTSSC
Pans    CTCESIAWFVNWINETN-TNIPELSSHYLCNTPPHYHGFPVRLFDTSSC
Bos     CTCESIAWFVNWINITH-TNISELSNHYLCNTPPQYHGYPVMLFDVSPC
Rattus  CTCESIAWFVTWLNQTH-TNIPELSTHYLCNTPQRYHGLPVKLFDTSSC
Mus     CTCESISWFVNWINQTH-TNISELSTHYLCNTPHHYYGFPLKLFDTSSC
Fugu    CTCESILWYATWLNNTNTTSVPDLAEQYTCNTPLTYFNRSIMTFDPLSC
Tetradon CTCESILWFVKWLNSTNTTSVPGLTEQYTCNTPLAYFNRSIMVFDPLSC
```

FIG. 2B

| Plasmid | PIC | % |
|---|---|---|
| WT TLR3 | - | 21 |
| WT TLR3 | + | 100 ± 2 |
| C242A | + | 89 ± 9 |
| C356A | + | 104 ± 4 |
| C242A/C356A | + | 104 ± 4 |
| C28A | + | 39 ± 13 |
| C37A | + | 30 ± 9 |
| C37S | | 28 ± 11 |
| C37M | + | 30 ± 10 |
| C95A | + | 30 ± 10 |
| C122A | | 33 ± 11 |
| C122S | + | 20 ± 9 |
| C122M | + | 18 ± 4 |
| C649A | | 20 ± 1 |
| C649S | + | 26 ± 2 |
| C649M | | 24 ± 2 |
| C651A | + | 20 ± 2 |
| C696A | | 22 ± 2 |
| C696S | + | 23 ± 1 |
| C696M | + | 24 ± 1 |
| C28A/C122A | + | 24 ± 2 |
| C37A/C651A | + | 23 ± .1 |

FIG. 3A

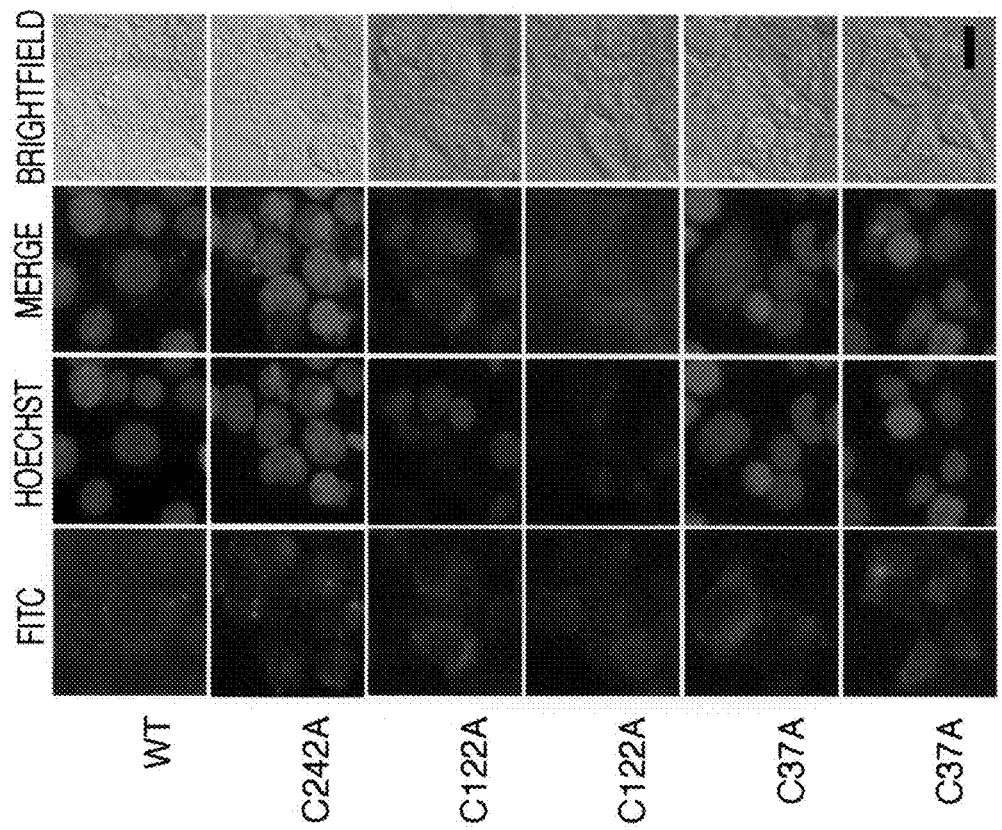

Loop 1

```
Homo      (333)  FTK-QSISLASL-PKID
Pan       (333)  FTK-QSISLASL-PKID
Bos       (334)  FTR-QSISLTSL-PKID
Rattus    (334)  FTK-QSVALASH-PNID
Mus       (334)  FTK-QSVSLASH-PNID
Takifugu  (331)  LVK-GHTS--AT-PIID
Tetraodon (333)  LVK-GHTS--AN-PVID
```

FIG. 4B

| Plasmid | P IC | % |
|---------|------|---|
| WT TLR3 | -    | 28 |
| WT TLR3 | +    | 100 ± 4 |
| L1-TCM  | +    | 103 ± 10 |
| L1-4M   | +    | 86 ± 4 |
| ΔL1     | +    | 81 ± 3 |

FIG. 4C

| | | |
|---|---|---|
| Homo | (545) | LWK-HANPGGPIY-FL |
| Pan | (545) | LWK-HANPGGPVY-FL |
| Canis | (1043) | LWK-HANPGGPVH-FL |
| Bos | (546) | LWK-HANPGGPVQ-FL |
| Rattus | (546) | LWK-HANPGGPVN-FL |
| Mus | (546) | LWK-RANPGGPVN-FL |
| Takifugu | (534) | LWK-NNNVGGPVM-FL |
| Tetraodon | (546) | LWK-NANPGGPVM-FL |

FIG. 5B

| Plasmid | P IC | % |
|---|---|---|
| WT TLR3 | − | 18 |
| WT TLR3 | + | 100 ± 7 |
| L2-TCM | + | 82 ± 5 |
| L2-Fugu | + | 75 ± 2 |
| ΔL2 | + | 19 ± 5 |

FIG. 5C

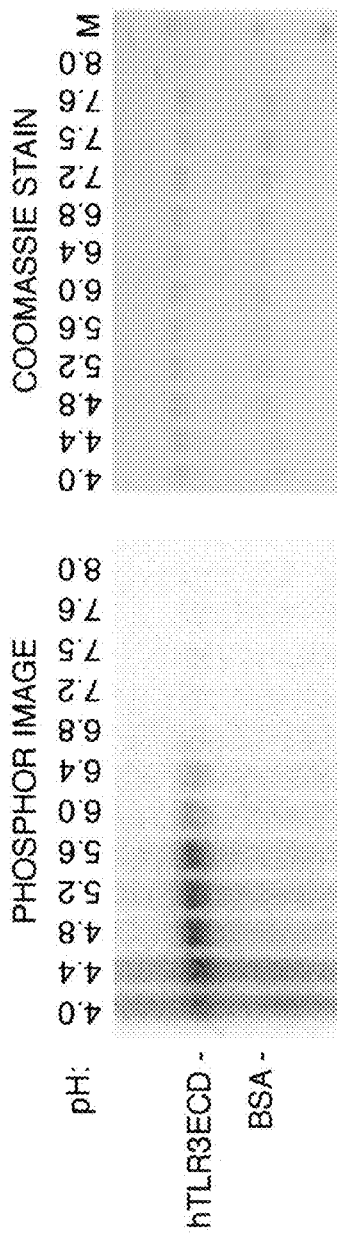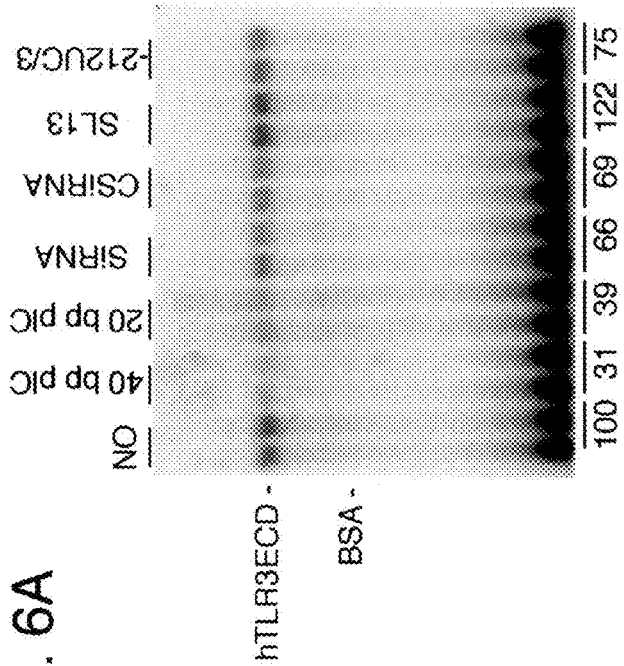
FIG. 6A
FIG. 6B
FIG. 6C

| Plasmid | PIC | Fold |
|---|---|---|
| WT TLR3 | − | 24 |
| WT TLR3 | + | 100 ± 9.7 |
| R65A* | + | 114 ± 16 |
| K89A* | + | 102 ± 7 |
| K117A* | + | 98 ± 6 |
| K137A* | + | 107 ± 12 |
| K139A* | + | 102 ± 9 |
| K147A* | | 134 ± 18 |
| K163A* | + | 85 ± 9 |
| K210A* | + | 93 ± 7 |
| R331A* | | 98 ± 19 |
| R394A* | + | 95 ± 9 |
| K418A* | + | 124 ± 12 |

| Plasmid | PIC | % |
|---|---|---|
| K493A* | + | 93 ± 15 |
| K589A | + | 83 ± 2 |
| K613A | + | 91 ± 6 |
| K627A | + | 93 ± 7 |
| R635A | + | 95 ± 5 |
| R643A | + | 104 ± 15 |
| R331A/K418A* | + | 100 ± 8 |
| R394A/K418A* | + | 52 ± 4 |
| R331A/R394A* | + | 85 ± 7 |
| K418A/K493A* | + | 74 ± 9 |
| K627A/K628A | + | 98 ± 3 |
| R331A/R394A/K418A* | + | 63 ± 7 |

FIG. 7A

| PLASMID | PIC | % |
|---|---|---|
| WT TLR3 | - | 8 |
| WT TLR3 | + | 100 ± 5 |
| H539E | + | 4 ± 2 |
| N541A | + | 5 ± 1 |
| N466A | + | 8 ± 1 |
| R489A | + | 16 ± 4 |
| N515A | + | 47 ± 4 |
| N516A | + | 36 ± 4 |
| N517A | + | 12 ± 1 |
| N540A | + | 8 ± 1 |
| R544A | + | 119 ± 10 |
| N572A | + | 55 ± 9 |

DLS analysis

| Buffer (pH) | MW (kDa) |
|---|---|
| 0.1 M NaOAc (4.8) | 192 ± 22 |
| 0.1 M NaOAc (5.2) | 189 ± 19 |
| 0.1 M NaOAc (5.6) | 230 ± 92 |
| 0.1 M NaOAc (6.0) | 172 ± 12 |
| PBS (7.5) | 178 ± 38 |

$V_e = 11.82$

Log MW = -0.19 ($V_e$) +7.54 = 196 kDa

| Plasmid | P IC | % |
|---|---|---|
| E442A | + | 62 ± 5 |
| E442D | + | 72 ± 7 |
| E442K | + | 25 ± 4 |
| K467A | + | 76 ± 7 |
| K467E | + | 60 ± 5 |
| K547A | + | 104 ± 8 |
| D575A | + | 87 ± 5 |
| E442K/K467E | + | 66 ± 3 |

| Compet. | Fold | % |
|---|---|---|
| None | - | 100 |
| WT TLR3 | 2 | 104 ± 7 |
|  | 6 | 96 ± 8 |
| ΔTIR | 2 | 30 ± 2 |
|  | 6 | 14 ± 1 |
| C37A | 2 | 81 ± 7 |
|  | 6 | 61 ± 1 |
| C696A | 2 | 84 ± 4 |
|  | 6 | 76 ± 3 |
| H539E | 2 | 34 ± 2 |
|  | 6 | 16 ± 1 |
| N466A | 2 | 47 ± 7 |
|  | 6 | 17 ± 2 |
| N517A | 2 | 51 ± 3 |
|  | 6 | 35 ± 4 |
| N540A | 2 | 98 ± 5 |
|  | 6 | 59 ± 1 |
| N541A | 2 | 60 ± 3 |
|  | 6 | 26 ± 1 |
| R489A | 2 | 36 ± 2 |
|  | 6 | 29 ± 4 |
| E442K | 2 | 68 ± 2 |
|  | 6 | 51 ± 3 |
| ΔL2 | 2 | 62 ± 7 |
|  | 6 | 56 ± 5 |

FIG. 10C

| Compet. | Fold | % |
|---|---|---|
| None | - | 100 |
| ΔTIR | 2 | 23 ± 2 |
|  | 6 | 12 ± 1 |
| K467EΔTIR | 2 | 51 ± 1 |
|  | 6 | 27 ± 1 |
| C37AΔTIR | 2 | 87 ± 7 |
|  | 6 | 96 ± 8 |
| C696AΔTIR | 2 | 83 ± 5 |
|  | 6 | 66 ± 2 |
| E442KΔTIR | 2 | 72 ± 7 |
|  | 6 | 55 ± 3 |
| ΔL2ΔTIR | 2 | 67 ± 6 |
|  | 6 | 70 ± 5 |

FIG. 10D

```
                               442                                         466 467
HOMO      (411)  ILNLTKNKISKIESDAFSWLGHLEVLDLGLNEIGQELTGWEWRGLENIFEIYLSYNKYL-
PAN       (411)  ILNLTKNKISKIESDAFSWLGHLEVLDLGLNEIFQELTGQEWRGLENIFEIYLSYNKYL-
CANIS     (909)  TLNLTKNKISKIESGAFSWLGHLQVLDLGLNEIGQELTGQEWRGLENIVEIYLSYNKYL-
BOS       (412)  LLNLTKNKISKIQSGAFSWLGHLEVLDLGLNEIGQELTGQEWRGLENIVEIYLSYNKYL-
RATTUS    (412)  TLNLTKNHISKIASGTFSWLGQLRILDLGLNEIEQELTGQEWRGLGNIFEIYLSYNKYL-
MUS       (412)  TLNLTKNHISKIANGTFSWLGQLRILDLGLNEIEQKLSGQEWRGLRNIFEIYLSYNKYL-
TAKIFUGU  (398)  KLNLTGAAVVQISPGGFSTLKSLTVLLLDSNFIKQTLTGREFEGLGQLEEIHMSLNFQKV
TETRAODON (410)  KLNLTGTAITQISPGGFSALRNLTVLLLDSNFIRQTFSGRELEGLAQLEEMHMSENYQKV 489   493                  515 517
HOMO      (470)  QLTRLSFALVPSLQRLMLRRVAIKN-VDSSPSPFQPLRNLTILDLSNINTANINDDMLEG
PAN       (470)  QLTRNSFALVPSLQRLMLRRVAIKN-VDSSPSPFQPLRNLTILDLSNINTANINDDMLEG
CANIS     (968)  QLTSSSFALISLTTLMIRRTAITN-VDSSPSPFHPLRNLNILDLSNINTANINDELLEG
BOS       (471)  ELTTNSFTSVPSLQRLMLTTVAIKN-VKCSPSPFTPLPNLVILDLSNINTANINDELLKG
RATTUS    (471)  QLTSKSFTLVPSLQRLMLRRVAIKS-VDISPSPFTPLYNLTILDLSNINTANLNEDLLEG
MUS       (471)  QLSTSSFALVPSLQRLMLRRVAIKN-VKISPSPFRPLRNLTILDLSNINTANINEDLLEG
TAKIFUGU  (458)  NLSSASFAAVPRLKVLTIGKSLTSTALNVDPSPFSPLVNLTFLDLSNINTANIRRTLLKG
TETRAODON (470)  NLSSASFVAVPSLRVLTIGKSLIISTALNLDPSPFSPLVHLSYLDLSNINTANIRRTLLKG 539 541 544                         572
HOMO      (529)  LEKLEIILDLQHNLARLWKHANPGGPIYFLKGLSHLHILNLESNGFDEIPVEVFKDLFEL
PAN       (529)  LEKLEIILDLQHMLARLWKHANPGGPVYFLKGLSHLHILNLESNGFDEIPVEVFKDLFEL
CANIS     (1027) LEKLEILDMQHNLAILWKHANPGGPVHFLKGLSHLHILNLESNGFEDIPAEVFKGLSEL
BOS       (530)  LEKLEILDLQHNLARLWKHANPGGPVQFLKGLFHLHILNLGSNGFDEIPVEAFKDLREL
RATTUS    (530)  LENLEILDLRQMLARLWKHANPGGPVNFLKGLSHLHILNLESNGFDEIPVKVFKNLFEL
MUS       (530)  LENLEILDFQHMLARLWKRANPGGPVNFLKGLSHLHILNLESNGLDEIPVGVFKNLFEL
TAKIFUGU  (518)  LVNLRVLKLQHMFATLWKNNNVGGPVMFLQDTLKLDTLLMKSNGLDEIPAGALRGLREL
TETRAODON (530)  LGRLKVLKLQHNFARLWKNANPGGPVMFLQDAVKLRTLLMDSNGLDEIPAEALRGLTEL
```

FIG. 12

1 mrqtlpciyf wggllpfgml casttkctv shevadcshl kltqvpddlp tnitvlnlth
61 nqlrrlpaan ftrysqltsl dvgfntiskl epelcqklpm lkvlnlqhne lsqlsdktfa
121 fctnltelhl msnsiqkikn npfvkqknli tldlshngls stklgtqvql enlqelllsn
181 nkiqalksee ldifansslk klelssnqik efspgcfhai grlfglflnn vqlgpsltek
241 lclelantsi rnlslsnsql sttsnttflg lkwtnltmld lsynnlnvvg ndsfawlpql
301 eyffleynni qhlfshslhg lfnvrylnlk rsftkqsisl aslpkiddfs fqwlkclehl
361 nmedndipgi ksnmftglin lkylslsnsf tslrtltnet fvslahsplh ilnltknkis
421 kiesdafswl ghlevldlgl neigqeltgq ewrglenife iylsynkylq ltrnsfalvp
481 slqrlmlrrv alknvdssps pfqplrnlti ldlsnnnian inddmlegle kleildlqhn
541 nlarlwkhan pggpiyflkg lshlhilnle sngfdeipve vfkdlfelki idlglnnlnt
601 lpasvfnnqv slkslnlqkn litsvekkvf gpafrnltel dmrfnpfdct cesiawfvnw
661 inethtnipe lsshylcntp phyhgfpvrl fdtssckdsa pfelffmint sillififiv
721 llihfegwri sfywnvsvhr vlgfkeidrq teqfeyaayi ihaykdkdwv wehfssmeke
781 dqslkfclee rdfeagvfel eaivnsikrs rkiifvithh llkdplckrf kvhhavqqai
841 eqnldsiilv fleeipdykl nhalclrrgm fkshcilnwp vqkerigafr hklqvalgsk
901 nsvh

SEQUENCE LISTING

<160> NUMBER OF SEQ ID NOS: 48

<210> SEQ ID NO 1
<211> LENGTH: 904
<212> TYPE: PRT
<213> ORGANISM: Homo sapiens

<400> SEQUENCE: 1

```
Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
```

```
            290                 295                 300
Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
                340                 345                 350

Trp Leu Lys Cys Leu Glu His Leu Asn Met Glu Asp Asn Asp Ile Pro
                355                 360                 365

Gly Ile Lys Ser Asn Met Phe Thr Gly Leu Ile Asn Leu Lys Tyr Leu
370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
                420                 425                 430

Leu Glu Val Leu Asp Leu Gly Leu Asn Glu Ile Gly Gln Glu Leu Thr
                435                 440                 445

Gly Gln Glu Trp Arg Gly Leu Glu Asn Ile Phe Glu Ile Tyr Leu Ser
450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
                500                 505                 510

Leu Ser Asn Asn Asn Ile Ala Asn Ile Asn Asp Asp Met Leu Glu Gly
                515                 520                 525

Leu Glu Lys Leu Glu Ile Leu Asp Leu Gln His Asn Asn Leu Ala Arg
                530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
                580                 585                 590

Leu Gly Leu Asn Asn Leu Asn Thr Leu Pro Ala Ser Val Phe Asn Asn
                595                 600                 605

Gln Val Ser Leu Lys Ser Leu Asn Leu Gln Lys Asn Leu Ile Thr Ser
610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
                675                 680                 685

Arg Leu Phe Asp Thr Ser Ser Cys Lys Asp Ser Ala Pro Phe Glu Leu
                690                 695                 700

Phe Phe Met Ile Asn Thr Ser Ile Leu Leu Ile Phe Ile Phe Ile Val
705                 710                 715                 720
```

```
Leu Leu Ile His Phe Glu Gly Trp Arg Ile Ser Phe Tyr Trp Asn Val
            725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
                820                 825                 830

His His Ala Val Gln Gln Ala Ile Glu Gln Asn Leu Asp Ser Ile Ile
            835                 840                 845

Leu Val Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
                900

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is His, Arg, or Asn.
<220> FEATURE:
<221> NAME/KEY: MISC_FEATURE
<222> LOCATION: (2)..(2)
<223> OTHER INFORMATION: X is Ala or Asn.
<220> FEATURE:
<221> NAME/KEY: MISC_FEATURE
<222> LOCATION: (4)..(4)
<223> OTHER INFORMATION: X is Pro or Val.
<220> FEATURE:
<221> NAME/KEY: MISC_FEATURE
<222> LOCATION: (8)..(8)
<223> OTHER INFORMATION: X is Ile or Val.
<220> FEATURE:
<221> NAME/KEY: MISC_FEATURE
<222> LOCATION: (9)..(9)
<223> OTHER INFORMATION: X is Tyr, His, Gln, Asn, or Met.

<400> SEQUENCE: 2

Xaa Xaa Asn Xaa Gly Gly Pro Xaa Xaa
1               5

<210> SEQ ID NO 3
<211> LENGTH: 14
<212> TYPE: PRT
<213> ORGANISM: Homo sapiens

<400> SEQUENCE: 3

Cys Thr Val Ser His Glu Val Ala Asp Cys Ser His Leu Lys
1               5                   10
```

```
<210> SEQ ID NO 4
<211> LENGTH: 38
<212> TYPE: PRT
<213> ORGANISM: Homo sapiens

<400> SEQUENCE: 4

Cys Thr Val Ser His Glu Val Ala Asp Cys Cys Gln Lys Leu Pro Met
1               5                   10                  15

Leu Lys Val Leu Asn Leu Gln His Asn Glu Leu Ser Gln Leu Ser Asp
            20                  25                  30

Lys Thr Phe Ala Phe Cys
            35

<210> SEQ ID NO 5
<211> LENGTH: 38
<212> TYPE: PRT
<213> ORGANISM: Pan troglodytes

<400> SEQUENCE: 5

Cys Thr Val Thr His Glu Val Ala Asp Cys Cys Gln Lys Leu Pro Met
1               5                   10                  15

Leu Lys Val Leu Asn Leu Gln His Asn Glu Leu Ser Gln Leu Ser Asp
            20                  25                  30

Lys Thr Phe Ala Phe Cys
            35

<210> SEQ ID NO 6
<211> LENGTH: 38
<212> TYPE: PRT
<213> ORGANISM: Bos taurus

<400> SEQUENCE: 6

Cys Thr Val Arg His Glu Val Ala Asp Cys Cys Gln Ser Leu Pro Trp
1               5                   10                  15

Leu Glu Ile Leu Asn Leu Gln His Asn Glu Ile Ser Gln Leu Ser Asp
            20                  25                  30

Lys Thr Phe Ile Phe Cys
            35

<210> SEQ ID NO 7
<211> LENGTH: 38
<212> TYPE: PRT
<213> ORGANISM: Rattus norvegicus

<400> SEQUENCE: 7

Cys Thr Val Arg Tyr Asn Val Ala Asp Cys Cys Gln Ile Leu Pro Leu
1               5                   10                  15

Leu Lys Val Leu Asn Leu Gln His Asn Glu Leu Ser Gln Ile Ser Asp
            20                  25                  30

Gln Thr Phe Ala Phe Cys
            35

<210> SEQ ID NO 8
<211> LENGTH: 38
<212> TYPE: PRT
<213> ORGANISM: Mus musculus

<400> SEQUENCE: 8

Cys Thr Val Arg Tyr Asn Val Ala Asp Cys Cys Gln Ile Leu Pro Leu
1               5                   10                  15

Leu Lys Val Leu Asn Leu Gln His Asn Glu Leu Ser Gln Ile Ser Asp
```

```
                  20                  25                  30

Gln Thr Phe Val Phe Cys
        35

<210> SEQ ID NO 9
<211> LENGTH: 38
<212> TYPE: PRT
<213> ORGANISM: Fugu rubripes

<400> SEQUENCE: 9

Cys Val Val Gln Gly Ser Ser Ala Asp Cys Cys Glu Thr Leu Pro Arg
1               5                   10                  15

Leu Gln Thr Leu Asp Val Ala His Asn Gln Val Leu Ala Leu Arg Glu
                20                  25                  30

Glu Asp Leu Ser Arg Cys
        35

<210> SEQ ID NO 10
<211> LENGTH: 38
<212> TYPE: PRT
<213> ORGANISM: Tetraodon nigroviridis

<400> SEQUENCE: 10

Cys Arg Val Gln Gly Asp Ser Ala Asp Cys Cys Glu Thr Leu Pro Arg
1               5                   10                  15

Leu Arg Thr Leu Asn Val Ala His Asn Gln Leu Leu Thr Leu Arg Glu
                20                  25                  30

Glu Asp Leu Asn Pro Cys
        35

<210> SEQ ID NO 11
<211> LENGTH: 48
<212> TYPE: PRT
<213> ORGANISM: Homo sapiens

<400> SEQUENCE: 11

Cys Thr Cys Glu Ser Ile Ala Trp Phe Val Asn Trp Ile Asn Glu Thr
1               5                   10                  15

His Thr Asn Ile Pro Glu Leu Ser Ser His Tyr Leu Cys Asn Thr Pro
                20                  25                  30

Pro His Tyr His Gly Phe Pro Val Arg Leu Phe Asp Thr Ser Ser Cys
        35                  40                  45

<210> SEQ ID NO 12
<211> LENGTH: 48
<212> TYPE: PRT
<213> ORGANISM: Pan troglodytes

<400> SEQUENCE: 12

Cys Thr Cys Glu Ser Ile Ala Trp Phe Val Asn Trp Ile Asn Glu Thr
1               5                   10                  15

Asn Thr Asn Ile Pro Glu Leu Ser Ser His Tyr Leu Cys Asn Thr Pro
                20                  25                  30

Pro His Tyr His Gly Phe Pro Val Arg Leu Phe Asp Thr Ser Ser Cys
        35                  40                  45

<210> SEQ ID NO 13
<211> LENGTH: 48
<212> TYPE: PRT
<213> ORGANISM: Bos taurus

<400> SEQUENCE: 13
```

```
Cys Thr Cys Glu Ser Ile Ala Trp Phe Val Asn Trp Ile Asn Ile Thr
1               5                   10                  15

His Thr Asn Ile Ser Glu Leu Ser Asn His Tyr Leu Cys Asn Thr Pro
            20                  25                  30

Pro Gln Tyr His Gly Tyr Pro Val Met Leu Phe Asp Val Ser Pro Cys
        35                  40                  45
```

<210> SEQ ID NO 14
<211> LENGTH: 48
<212> TYPE: PRT
<213> ORGANISM: Rattus norvegicus

<400> SEQUENCE: 14

```
Cys Thr Cys Glu Ser Ile Ala Trp Phe Val Thr Trp Leu Asn Gln Thr
1               5                   10                  15

His Thr Asn Ile Pro Glu Leu Ser Thr His Tyr Leu Cys Asn Thr Pro
            20                  25                  30

Gln Arg Tyr His Gly Leu Pro Val Lys Leu Phe Asp Thr Ser Ser Cys
        35                  40                  45
```

<210> SEQ ID NO 15
<211> LENGTH: 48
<212> TYPE: PRT
<213> ORGANISM: Mus musculus

<400> SEQUENCE: 15

```
Cys Thr Cys Glu Ser Ile Ser Trp Phe Val Trp Ile Asn Gln Thr
1               5                   10                  15

His Thr Asn Ile Ser Glu Leu Ser Thr His Tyr Leu Cys Asn Thr Pro
            20                  25                  30

His His Tyr Tyr Gly Phe Pro Leu Lys Leu Phe Asp Thr Ser Ser Cys
        35                  40                  45
```

<210> SEQ ID NO 16
<211> LENGTH: 49
<212> TYPE: PRT
<213> ORGANISM: Fugu rubripes

<400> SEQUENCE: 16

```
Cys Thr Cys Glu Ser Ile Leu Trp Tyr Ala Thr Trp Leu Asn Asn Thr
1               5                   10                  15

Asn Thr Thr Ser Val Pro Asp Leu Ala Glu Gln Tyr Thr Cys Asn Thr
            20                  25                  30

Pro Leu Thr Tyr Phe Asn Arg Ser Ile Met Thr Phe Asp Pro Leu Ser
        35                  40                  45

Cys
```

<210> SEQ ID NO 17
<211> LENGTH: 49
<212> TYPE: PRT
<213> ORGANISM: Tetraodon nigroviridis

<400> SEQUENCE: 17

```
Cys Thr Cys Glu Ser Ile Leu Trp Phe Val Lys Trp Leu Asn Ser Thr
1               5                   10                  15

Asn Thr Ser Val Pro Gly Leu Thr Glu Gln Tyr Thr Cys Asn Thr
            20                  25                  30

Pro Leu Ala Tyr Phe Asn Arg Ser Ile Met Val Phe Asp Pro Leu Ser
        35                  40                  45
```

Cys

```
<210> SEQ ID NO 18
<211> LENGTH: 15
<212> TYPE: PRT
<213> ORGANISM: Homo sapiens

<400> SEQUENCE: 18
```

Phe Thr Lys Gln Ser Ile Ser Leu Ala Ser Leu Pro Lys Ile Asp
1               5                   10                  15

```
<210> SEQ ID NO 19
<211> LENGTH: 15
<212> TYPE: PRT
<213> ORGANISM: Pan troglodytes

<400> SEQUENCE: 19
```

Phe Thr Lys Gln Ser Ile Ser Leu Ala Ser Leu Pro Lys Ile Asp
1               5                   10                  15

```
<210> SEQ ID NO 20
<211> LENGTH: 15
<212> TYPE: PRT
<213> ORGANISM: Bos taurus

<400> SEQUENCE: 20
```

Phe Thr Arg Gln Ser Ile Ser Leu Thr Ser Leu Pro Lys Ile Asp
1               5                   10                  15

```
<210> SEQ ID NO 21
<211> LENGTH: 15
<212> TYPE: PRT
<213> ORGANISM: Rattus norvegicus

<400> SEQUENCE: 21
```

Phe Thr Lys Gln Ser Val Ala Leu Ala Ser His Pro Asn Ile Asp
1               5                   10                  15

```
<210> SEQ ID NO 22
<211> LENGTH: 15
<212> TYPE: PRT
<213> ORGANISM: Mus musculus

<400> SEQUENCE: 22
```

Phe Thr Lys Gln Ser Val Ser Leu Ala Ser His Pro Asn Ile Asp
1               5                   10                  15

```
<210> SEQ ID NO 23
<211> LENGTH: 13
<212> TYPE: PRT
<213> ORGANISM: Fugu rubripes

<400> SEQUENCE: 23
```

Leu Val Lys Gly His Thr Ser Ala Thr Pro Ile Ile Asp
1               5                   10

```
<210> SEQ ID NO 24
<211> LENGTH: 13
<212> TYPE: PRT
<213> ORGANISM: Tetraodon nigroviridis

<400> SEQUENCE: 24
```

Leu Val Lys Gly His Thr Ser Ala Asn Pro Val Ile Asp
1               5                   10

```
<210> SEQ ID NO 25
<211> LENGTH: 14
<212> TYPE: PRT
<213> ORGANISM: Homo sapiens

<400> SEQUENCE: 25

Leu Trp Lys His Ala Asn Pro Gly Gly Pro Ile Tyr Phe Leu
1               5                   10

<210> SEQ ID NO 26
<211> LENGTH: 14
<212> TYPE: PRT
<213> ORGANISM: Pan troglodytes

<400> SEQUENCE: 26

Leu Trp Lys His Ala Asn Pro Gly Gly Pro Val Tyr Phe Leu
1               5                   10

<210> SEQ ID NO 27
<211> LENGTH: 14
<212> TYPE: PRT
<213> ORGANISM: Canis familiaris

<400> SEQUENCE: 27

Leu Trp Lys His Ala Asn Pro Gly Gly Pro Val His Phe Leu
1               5                   10

<210> SEQ ID NO 28
<211> LENGTH: 14
<212> TYPE: PRT
<213> ORGANISM: Bos taurus

<400> SEQUENCE: 28

Leu Trp Lys His Ala Asn Pro Gly Gly Pro Val Gln Phe Leu
1               5                   10

<210> SEQ ID NO 29
<211> LENGTH: 14
<212> TYPE: PRT
<213> ORGANISM: Rattus norvegicus

<400> SEQUENCE: 29

Leu Trp Lys His Ala Asn Pro Gly Gly Pro Val Asn Phe Leu
1               5                   10

<210> SEQ ID NO 30
<211> LENGTH: 14
<212> TYPE: PRT
<213> ORGANISM: Mus musculus

<400> SEQUENCE: 30

Leu Trp Lys Arg Ala Asn Pro Gly Gly Pro Val Asn Phe Leu
1               5                   10

<210> SEQ ID NO 31
<211> LENGTH: 14
<212> TYPE: PRT
<213> ORGANISM: Fugu rubripes

<400> SEQUENCE: 31

Leu Trp Lys Asn Asn Asn Val Gly Gly Pro Val Met Phe Leu
1               5                   10

<210> SEQ ID NO 32
<211> LENGTH: 14
<212> TYPE: PRT
```

-continued

<213> ORGANISM: Tetraodon nigroviridis

<400> SEQUENCE: 32

Leu Trp Lys Asn Ala Asn Pro Gly Gly Pro Val Met Phe Leu
1               5                   10

<210> SEQ ID NO 33
<211> LENGTH: 178
<212> TYPE: PRT
<213> ORGANISM: Homo sapiens

<400> SEQUENCE: 33

Ile Leu Asn Leu Thr Lys Asn Lys Ile Ser Lys Ile Glu Ser Asp Ala
1               5                   10                  15

Phe Ser Trp Leu Gly His Leu Glu Val Leu Asp Leu Gly Leu Asn Glu
            20                  25                  30

Ile Gly Gln Glu Leu Thr Gly Gln Glu Trp Arg Gly Leu Glu Asn Ile
        35                  40                  45

Phe Glu Ile Tyr Leu Ser Tyr Asn Lys Tyr Leu Gln Leu Thr Arg Asn
    50                  55                  60

Ser Phe Ala Leu Val Pro Ser Leu Gln Arg Leu Met Leu Arg Arg Val
65                  70                  75                  80

Ala Leu Lys Asn Val Asp Ser Ser Pro Ser Pro Phe Gln Pro Leu Arg
                85                  90                  95

Asn Leu Thr Ile Leu Asp Leu Ser Asn Asn Asn Ile Ala Asn Ile Asn
            100                 105                 110

Asp Asp Met Leu Glu Gly Leu Glu Lys Leu Glu Ile Leu Asp Leu Gln
        115                 120                 125

His Asn Asn Leu Ala Arg Leu Trp Lys His Ala Asn Pro Gly Gly Pro
    130                 135                 140

Ile Tyr Phe Leu Lys Gly Leu Ser His Leu His Ile Leu Asn Leu Glu
145                 150                 155                 160

Ser Asn Gly Phe Asp Glu Ile Pro Val Glu Val Phe Lys Asp Leu Phe
                165                 170                 175

Glu Leu

<210> SEQ ID NO 34
<211> LENGTH: 178
<212> TYPE: PRT
<213> ORGANISM: Pan troglodytes

<400> SEQUENCE: 34

Ile Leu Asn Leu Thr Lys Asn Lys Ile Ser Lys Ile Glu Ser Asp Ala
1               5                   10                  15

Phe Ser Trp Leu Gly His Leu Glu Val Leu Asp Leu Gly Leu Asn Glu
            20                  25                  30

Ile Gly Gln Glu Leu Thr Gly Gln Glu Trp Arg Gly Leu Glu Asn Ile
        35                  40                  45

Phe Glu Ile Tyr Leu Ser Tyr Asn Lys Tyr Leu Gln Leu Thr Arg Asn
    50                  55                  60

Ser Phe Ala Leu Val Pro Ser Leu Gln Arg Leu Met Leu Arg Arg Val
65                  70                  75                  80

Ala Leu Lys Asn Val Asp Ser Ser Pro Ser Pro Phe Gln Pro Leu Arg
                85                  90                  95

Asn Leu Thr Ile Leu Asp Leu Ser Asn Asn Asn Ile Ala Asn Ile Asn
            100                 105                 110

Asp Asp Met Leu Glu Gly Leu Glu Lys Leu Glu Ile Leu Asp Leu Gln

```
                    115                 120                 125
His Asn Asn Leu Ala Arg Leu Trp Lys His Ala Asn Pro Gly Gly Pro
    130                 135                 140

Val Tyr Phe Leu Lys Gly Leu Ser His Leu His Ile Leu Asn Leu Glu
145                 150                 155                 160

Ser Asn Gly Phe Asp Glu Ile Pro Val Glu Val Phe Lys Asp Leu Phe
                165                 170                 175

Glu Leu

<210> SEQ ID NO 35
<211> LENGTH: 178
<212> TYPE: PRT
<213> ORGANISM: Canis familiaris

<400> SEQUENCE: 35

Thr Leu Asn Leu Thr Lys Asn Lys Ile Ser Lys Ile Glu Ser Gly Ala
1               5                   10                  15

Phe Ser Trp Leu Gly His Leu Gln Val Leu Asp Leu Gly Leu Asn Glu
                20                  25                  30

Ile Gly Gln Glu Leu Thr Gly Gln Glu Trp Arg Gly Leu Glu Asn Ile
            35                  40                  45

Val Glu Ile Tyr Leu Ser Tyr Asn Lys Tyr Leu Gln Leu Thr Ser Ser
    50                  55                  60

Ser Phe Ala Leu Ile Pro Ser Leu Arg Arg Leu Met Leu Arg Arg Thr
65                  70                  75                  80

Ala Leu Arg Asn Val Asp Ser Ser Pro Ser Phe His Pro Leu Arg
                85                  90                  95

Asn Leu Asn Ile Leu Asp Leu Ser Asn Asn Asn Ile Ala Asn Ile Asn
                100                 105                 110

Asp Glu Leu Leu Glu Gly Leu Glu Lys Leu Glu Ile Leu Asp Met Gln
            115                 120                 125

His Asn Asn Leu Ala Arg Leu Trp Lys His Ala Asn Pro Gly Gly Pro
    130                 135                 140

Val His Phe Leu Lys Gly Leu Ser His Leu His Ile Leu Asn Leu Glu
145                 150                 155                 160

Ser Asn Gly Phe Asp Glu Ile Pro Ala Glu Val Phe Lys Gly Leu Ser
                165                 170                 175

Glu Leu

<210> SEQ ID NO 36
<211> LENGTH: 178
<212> TYPE: PRT
<213> ORGANISM: Bos taurus

<400> SEQUENCE: 36

Leu Leu Asn Leu Thr Lys Asn Lys Ile Ser Lys Ile Gln Ser Gly Ala
1               5                   10                  15

Phe Ser Trp Leu Gly His Leu Glu Val Leu Asp Leu Gly Leu Asn Glu
                20                  25                  30

Ile Gly Gln Glu Leu Thr Gly Gln Glu Trp Arg Gly Leu Asp Asn Ile
            35                  40                  45

Val Glu Ile Tyr Leu Ser Tyr Asn Lys Tyr Leu Glu Leu Thr Thr Asn
    50                  55                  60

Ser Phe Thr Ser Val Pro Ser Leu Gln Arg Leu Met Leu Arg Arg Val
65                  70                  75                  80

Ala Leu Lys Asn Val Asp Cys Ser Pro Ser Pro Phe Arg Pro Leu Pro
```

```
                    85                  90                  95
Asn Leu Val Ile Leu Asp Leu Ser Asn Asn Ile Ala Asn Ile Asn
                100                 105                 110

Asp Glu Leu Leu Lys Gly Leu Glu Lys Leu Glu Ile Leu Asp Leu Gln
                115                 120                 125

His Asn Asn Leu Ala Arg Leu Trp Lys His Ala Asn Pro Gly Gly Pro
                130                 135                 140

Val Gln Phe Leu Lys Gly Leu Phe His Leu His Ile Leu Asn Leu Gly
145                 150                 155                 160

Ser Asn Gly Phe Asp Glu Ile Pro Val Glu Ala Phe Lys Asp Leu Arg
                165                 170                 175

Glu Leu

<210> SEQ ID NO 37
<211> LENGTH: 178
<212> TYPE: PRT
<213> ORGANISM: Rattus norvegicus

<400> SEQUENCE: 37

Thr Leu Asn Leu Thr Lys Asn His Ile Ser Lys Ile Ala Ser Gly Thr
1               5                   10                  15

Phe Ser Trp Leu Gly Gln Leu Arg Ile Leu Asp Leu Gly Leu Asn Glu
                20                  25                  30

Ile Glu Gln Glu Leu Thr Gly Gln Glu Trp Arg Gly Leu Gly Asn Ile
            35                  40                  45

Phe Glu Ile Tyr Leu Ser Tyr Asn Lys Tyr Leu Gln Leu Thr Ser Lys
        50                  55                  60

Ser Phe Thr Leu Val Pro Ser Leu Gln Arg Leu Met Leu Arg Arg Val
65                  70                  75                  80

Ala Leu Lys Ser Val Asp Ile Ser Pro Ser Pro Phe Arg Pro Leu Tyr
                85                  90                  95

Asn Leu Thr Ile Leu Asp Leu Ser Asn Asn Ile Ala Asn Leu Asn
                100                 105                 110

Glu Asp Leu Leu Glu Gly Leu Glu Asn Leu Glu Ile Leu Asp Phe Gln
                115                 120                 125

His Asn Asn Leu Ala Arg Leu Trp Lys His Ala Asn Pro Gly Gly Pro
                130                 135                 140

Val Asn Phe Leu Lys Gly Leu Ser His Leu His Ile Leu Asn Leu Glu
145                 150                 155                 160

Ser Asn Gly Leu Asp Glu Ile Pro Val Lys Val Phe Lys Asn Leu Phe
                165                 170                 175

Glu Leu

<210> SEQ ID NO 38
<211> LENGTH: 178
<212> TYPE: PRT
<213> ORGANISM: Mus musculus

<400> SEQUENCE: 38

Thr Leu Asn Leu Thr Lys Asn His Ile Ser Lys Ile Ala Asn Gly Thr
1               5                   10                  15

Phe Ser Trp Leu Gly Gln Leu Arg Ile Leu Asp Leu Gly Leu Asn Glu
                20                  25                  30

Ile Glu Gln Lys Leu Ser Gly Gln Glu Trp Arg Gly Leu Arg Asn Ile
            35                  40                  45

Phe Glu Ile Tyr Leu Ser Tyr Asn Lys Tyr Leu Gln Leu Ser Thr Ser
```

```
                 50                  55                  60
Ser Phe Ala Leu Val Pro Ser Leu Gln Arg Leu Met Leu Arg Arg Val
 65                  70                  75                  80

Ala Leu Lys Asn Val Asp Ile Ser Pro Ser Pro Phe Arg Pro Leu Arg
                 85                  90                  95

Asn Leu Thr Ile Leu Asp Leu Ser Asn Asn Asn Ile Ala Asn Ile Asn
                100                 105                 110

Glu Asp Leu Leu Glu Gly Leu Glu Asn Leu Gly Ile Leu Asp Phe Gln
                115                 120                 125

His Asn Asn Leu Ala Arg Leu Trp Lys Arg Ala Asn Pro Gly Gly Pro
                130                 135                 140

Val Asn Phe Leu Lys Gly Leu Ser His Leu His Ile Leu Asn Leu Glu
145                 150                 155                 160

Ser Asn Gly Leu Asp Glu Ile Pro Val Gly Val Phe Lys Asn Leu Phe
                165                 170                 175

Glu Leu

<210> SEQ ID NO 39
<211> LENGTH: 180
<212> TYPE: PRT
<213> ORGANISM: Fugu rubripes

<400> SEQUENCE: 39

Lys Leu Asn Leu Thr Gly Ala Ala Val Val Gln Ile Ser Pro Gly Gly
 1                   5                  10                  15

Phe Ser Thr Leu Lys Ser Leu Thr Val Leu Leu Leu Asp Ser Asn Phe
                 20                  25                  30

Ile Lys Gln Thr Leu Thr Gly Arg Glu Phe Glu Gly Leu Gly Gln Leu
                 35                  40                  45

Glu Glu Ile His Met Ser Leu Asn Phe Gln Lys Val Asn Leu Ser Ser
                 50                  55                  60

Ala Ser Phe Ala Ala Val Pro Arg Leu Lys Val Leu Thr Leu Gly Lys
 65                  70                  75                  80

Ser Leu Thr Ser Thr Ala Leu Asn Val Asp Pro Ser Pro Phe Ser Pro
                 85                  90                  95

Leu Val Asn Leu Thr Phe Leu Asp Leu Ser Asn Asn Asn Ile Ala Asn
                100                 105                 110

Ile Arg Arg Thr Leu Leu Lys Gly Leu Val Asn Leu Arg Val Leu Lys
                115                 120                 125

Leu Gln His Asn Asn Phe Ala Arg Leu Trp Lys Asn Asn Asn Val Gly
                130                 135                 140

Gly Pro Val Met Phe Leu Gln Asp Thr Leu Lys Leu Lys Thr Leu Leu
145                 150                 155                 160

Met Asp Ser Asn Gly Leu Asp Glu Ile Pro Ala Gly Ala Leu Arg Gly
                165                 170                 175

Leu Arg Glu Leu
            180

<210> SEQ ID NO 40
<211> LENGTH: 180
<212> TYPE: PRT
<213> ORGANISM: Tetraodon nigroviridis

<400> SEQUENCE: 40

Lys Leu Asn Leu Thr Gly Thr Ala Ile Thr Gln Ile Ser Pro Gly Gly
 1                   5                  10                  15
```

```
Phe Ser Ala Leu Arg Asn Leu Thr Val Leu Leu Asp Ser Asn Phe
             20                  25                  30

Ile Arg Gln Thr Phe Ser Gly Arg Glu Leu Glu Gly Leu Ala Gln Leu
        35                  40                  45

Glu Glu Met His Met Ser Leu Asn Tyr Gln Lys Val Asn Leu Ser Ser
 50                  55                  60

Ala Ser Phe Val Ala Val Pro Ser Leu Arg Val Leu Thr Leu Gly Lys
 65                  70                  75                  80

Ser Leu Ile Ser Thr Ala Leu Asn Leu Asp Pro Ser Pro Phe Ser Pro
                 85                  90                  95

Leu Val His Leu Ser Tyr Leu Asp Leu Ser Asn Asn Asn Ile Ala Asn
            100                 105                 110

Ile Arg Arg Thr Leu Leu Lys Gly Leu Gly Arg Leu Lys Val Leu Lys
        115                 120                 125

Leu Gln His Asn Asn Phe Ala Arg Leu Trp Lys Asn Ala Asn Pro Gly
    130                 135                 140

Gly Pro Val Met Phe Leu Gln Asp Ala Val Lys Leu Arg Thr Leu Leu
145                 150                 155                 160

Met Asp Ser Asn Gly Leu Asp Glu Ile Pro Ala Glu Ala Leu Arg Gly
                165                 170                 175

Leu Thr Glu Leu
            180

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

His Ala Asn Pro Gly Gly Ile Tyr
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is a naturally or nonnaturally occurring
      amino acid
<220> FEATURE:
<221> NAME/KEY: MISC_FEATURE
<222> LOCATION: (2)..(2)
<223> OTHER INFORMATION: X is a naturally or nonnaturally occurring
      amino acid
<220> FEATURE:
<221> NAME/KEY: MISC_FEATURE
<222> LOCATION: (4)..(4)
<223> OTHER INFORMATION: X is a naturally or nonnaturally occurring
      amino acid
<220> FEATURE:
<221> NAME/KEY: MISC_FEATURE
<222> LOCATION: (8)..(8)
<223> OTHER INFORMATION: X is a naturally or nonnaturally occurring
      amino acid
<220> FEATURE:
<221> NAME/KEY: MISC_FEATURE
<222> LOCATION: (9)..(9)
<223> OTHER INFORMATION: X is a naturally or nonnaturally occurring
      amino acid

<400> SEQUENCE: 42
```

```
Xaa Xaa Asn Xaa Gly Gly Pro Xaa Xaa
1               5
```

```
<210> SEQ ID NO 43
<211> LENGTH: 904
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (28)..(28)
<223> OTHER INFORMATION: X is C or A
<220> FEATURE:
<221> NAME/KEY: MISC_FEATURE
<222> LOCATION: (37)..(37)
<223> OTHER INFORMATION: X is C, A, S, or M
<220> FEATURE:
<221> NAME/KEY: MISC_FEATURE
<222> LOCATION: (65)..(65)
<223> OTHER INFORMATION: X is R or A
<220> FEATURE:
<221> NAME/KEY: MISC_FEATURE
<222> LOCATION: (89)..(89)
<223> OTHER INFORMATION: X is K or A
<220> FEATURE:
<221> NAME/KEY: MISC_FEATURE
<222> LOCATION: (95)..(95)
<223> OTHER INFORMATION: X is C or A
<220> FEATURE:
<221> NAME/KEY: MISC_FEATURE
<222> LOCATION: (117)..(117)
<223> OTHER INFORMATION: X is K or A
<220> FEATURE:
<221> NAME/KEY: MISC_FEATURE
<222> LOCATION: (122)..(122)
<223> OTHER INFORMATION: X is C, A, S, or M
<220> FEATURE:
<221> NAME/KEY: MISC_FEATURE
<222> LOCATION: (137)..(137)
<223> OTHER INFORMATION: X is K or A
<220> FEATURE:
<221> NAME/KEY: MISC_FEATURE
<222> LOCATION: (139)..(139)
<223> OTHER INFORMATION: X is K or A
<220> FEATURE:
<221> NAME/KEY: MISC_FEATURE
<222> LOCATION: (147)..(147)
<223> OTHER INFORMATION: X is K or A
<220> FEATURE:
<221> NAME/KEY: MISC_FEATURE
<222> LOCATION: (163)..(163)
<223> OTHER INFORMATION: X is K or A
<220> FEATURE:
<221> NAME/KEY: MISC_FEATURE
<222> LOCATION: (210)..(210)
<223> OTHER INFORMATION: X is K or A
<220> FEATURE:
<221> NAME/KEY: MISC_FEATURE
<222> LOCATION: (242)..(242)
<223> OTHER INFORMATION: X is C or A
<220> FEATURE:
<221> NAME/KEY: MISC_FEATURE
<222> LOCATION: (331)..(331)
<223> OTHER INFORMATION: X is R or A
<220> FEATURE:
<221> NAME/KEY: MISC_FEATURE
<222> LOCATION: (356)..(356)
<223> OTHER INFORMATION: X is C or A
<220> FEATURE:
<221> NAME/KEY: MISC_FEATURE
<222> LOCATION: (394)..(394)
<223> OTHER INFORMATION: X is R or A
<220> FEATURE:
<221> NAME/KEY: MISC_FEATURE
<222> LOCATION: (418)..(418)
<223> OTHER INFORMATION: X is K or A
<220> FEATURE:
```

```
<221> NAME/KEY: MISC_FEATURE
<222> LOCATION: (442)..(442)
<223> OTHER INFORMATION: X is E, A, D, or K
<220> FEATURE:
<221> NAME/KEY: MISC_FEATURE
<222> LOCATION: (466)..(466)
<223> OTHER INFORMATION: X is N or A
<220> FEATURE:
<221> NAME/KEY: MISC_FEATURE
<222> LOCATION: (467)..(467)
<223> OTHER INFORMATION: X is K, A, or E
<220> FEATURE:
<221> NAME/KEY: MISC_FEATURE
<222> LOCATION: (489)..(489)
<223> OTHER INFORMATION: X is R or A
<220> FEATURE:
<221> NAME/KEY: MISC_FEATURE
<222> LOCATION: (493)..(493)
<223> OTHER INFORMATION: X is K or A
<220> FEATURE:
<221> NAME/KEY: MISC_FEATURE
<222> LOCATION: (515)..(515)
<223> OTHER INFORMATION: X is N or A
<220> FEATURE:
<221> NAME/KEY: MISC_FEATURE
<222> LOCATION: (516)..(516)
<223> OTHER INFORMATION: X is N or A
<220> FEATURE:
<221> NAME/KEY: MISC_FEATURE
<222> LOCATION: (517)..(517)
<223> OTHER INFORMATION: X is N or A
<220> FEATURE:
<221> NAME/KEY: MISC_FEATURE
<222> LOCATION: (539)..(539)
<223> OTHER INFORMATION: X is H or E
<220> FEATURE:
<221> NAME/KEY: MISC_FEATURE
<222> LOCATION: (540)..(540)
<223> OTHER INFORMATION: X is N or A
<220> FEATURE:
<221> NAME/KEY: MISC_FEATURE
<222> LOCATION: (541)..(541)
<223> OTHER INFORMATION: X is N or A
<220> FEATURE:
<221> NAME/KEY: MISC_FEATURE
<222> LOCATION: (544)..(544)
<223> OTHER INFORMATION: X is R or A
<220> FEATURE:
<221> NAME/KEY: MISC_FEATURE
<222> LOCATION: (547)..(547)
<223> OTHER INFORMATION: X is K or A
<220> FEATURE:
<221> NAME/KEY: MISC_FEATURE
<222> LOCATION: (572)..(572)
<223> OTHER INFORMATION: X is N or A
<220> FEATURE:
<221> NAME/KEY: MISC_FEATURE
<222> LOCATION: (575)..(575)
<223> OTHER INFORMATION: X is D or A
<220> FEATURE:
<221> NAME/KEY: MISC_FEATURE
<222> LOCATION: (589)..(589)
<223> OTHER INFORMATION: X is K or A
<220> FEATURE:
<221> NAME/KEY: MISC_FEATURE
<222> LOCATION: (613)..(613)
<223> OTHER INFORMATION: X is K or A
<220> FEATURE:
<221> NAME/KEY: MISC_FEATURE
<222> LOCATION: (627)..(627)
<223> OTHER INFORMATION: X is K or A
<220> FEATURE:
<221> NAME/KEY: MISC_FEATURE
<222> LOCATION: (635)..(635)
<223> OTHER INFORMATION: X is R or A
<220> FEATURE:
<221> NAME/KEY: MISC_FEATURE
<222> LOCATION: (643)..(643)
<223> OTHER INFORMATION: X is R or A
<220> FEATURE:
```

```
<221> NAME/KEY: MISC_FEATURE
<222> LOCATION: (649)..(649)
<223> OTHER INFORMATION: X is C, A, S, or M
<220> FEATURE:
<221> NAME/KEY: MISC_FEATURE
<222> LOCATION: (651)..(651)
<223> OTHER INFORMATION: X is C or A
<220> FEATURE:
<221> NAME/KEY: MISC_FEATURE
<222> LOCATION: (696)..(696)
<223> OTHER INFORMATION: X is C, A, S, or M

<400> SEQUENCE: 43
```

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Xaa Thr Val Ser His
            20                  25                  30

Glu Val Ala Asp Xaa Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Xaa Leu Pro Ala Ala Asn Phe Thr Arg Tyr Ser Gln Leu Thr Ser Leu
65                  70                  75                  80

Asp Val Gly Phe Asn Thr Ile Ser Xaa Leu Glu Pro Glu Leu Xaa Gln
                85                  90                  95

Lys Leu Pro Met Leu Lys Val Leu Asn Leu Gln His Asn Glu Leu Ser
            100                 105                 110

Gln Leu Ser Asp Xaa Thr Phe Ala Phe Xaa Thr Asn Leu Thr Glu Leu
        115                 120                 125

His Leu Met Ser Asn Ser Ile Gln Xaa Ile Xaa Asn Asn Pro Phe Val
    130                 135                 140

Lys Gln Xaa Asn Leu Ile Thr Leu Asp Leu Ser His Asn Gly Leu Ser
145                 150                 155                 160

Ser Thr Xaa Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Xaa Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Xaa Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Xaa Ser Phe Thr Lys Gln
                325                 330                 335

Ser Ile Ser Leu Ala Ser Leu Pro Lys Ile Asp Asp Phe Ser Phe Gln
            340                 345                 350

```
Trp Leu Lys Xaa Leu Glu His Leu Asn Met Glu Asp Asn Asp Ile Pro
            355                 360                 365

Gly Ile Lys Ser Asn Met Phe Thr Gly Leu Ile Asn Leu Lys Tyr Leu
370                 375                 380

Ser Leu Ser Asn Ser Phe Thr Ser Leu Xaa Thr Leu Thr Asn Glu Thr
385                 390                 395                 400

Phe Val Ser Leu Ala His Ser Pro Leu His Ile Leu Asn Leu Thr Lys
                405                 410                 415

Asn Xaa Ile Ser Lys Ile Glu Ser Asp Ala Phe Ser Trp Leu Gly His
            420                 425                 430

Leu Glu Val Leu Asp Leu Gly Leu Asn Xaa Ile Gly Gln Glu Leu Thr
            435                 440                 445

Gly Gln Glu Trp Arg Gly Leu Glu Asn Ile Phe Glu Ile Tyr Leu Ser
450                 455                 460

Tyr Xaa Xaa Tyr Leu Gln Leu Thr Arg Asn Ser Phe Ala Leu Val Pro
465                 470                 475                 480

Ser Leu Gln Arg Leu Met Leu Arg Xaa Val Ala Leu Xaa Asn Val Asp
                485                 490                 495

Ser Ser Pro Ser Pro Phe Gln Pro Leu Arg Asn Leu Thr Ile Leu Asp
            500                 505                 510

Leu Ser Xaa Xaa Xaa Ile Ala Asn Ile Asn Asp Asp Met Leu Glu Gly
            515                 520                 525

Leu Glu Lys Leu Glu Ile Leu Asp Leu Gln Xaa Xaa Xaa Leu Ala Xaa
530                 535                 540

Leu Trp Xaa His Ala Asn Pro Gly Gly Pro Ile Tyr Phe Leu Lys Gly
545                 550                 555                 560

Leu Ser His Leu His Ile Leu Asn Leu Glu Ser Xaa Gly Phe Xaa Glu
                565                 570                 575

Ile Pro Val Glu Val Phe Lys Asp Leu Phe Glu Leu Xaa Ile Ile Asp
                580                 585                 590

Leu Gly Leu Asn Asn Leu Asn Thr Leu Pro Ala Ser Val Phe Asn Asn
            595                 600                 605

Gln Val Ser Leu Xaa Ser Leu Asn Leu Gln Lys Asn Leu Ile Thr Ser
610                 615                 620

Val Glu Xaa Lys Val Phe Gly Pro Ala Phe Xaa Asn Leu Thr Glu Leu
625                 630                 635                 640

Asp Met Xaa Phe Asn Pro Phe Asp Xaa Thr Xaa Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
            675                 680                 685

Arg Leu Phe Asp Thr Ser Ser Xaa Lys Asp Ser Ala Pro Phe Glu Leu
690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
770                 775                 780
```

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
            805                 810                 815

Ile Thr His His Leu Leu Lys Asp Pro Leu Cys Lys Arg Phe Lys Val
            820                 825                 830

His His Ala Val Gln Gln Ala Ile Gln Asn Leu Asp Ser Ile Ile
        835                 840                 845

Leu Val Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
                900

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Ser Ile Ser Leu Ala Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Cys Cys Pro Gly Cys Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Gln Ser Ile Ser Leu Ala Ser Leu
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Gln Ser Thr Ala Leu Thr Ser His
1               5

<210> SEQ ID NO 48
<211> LENGTH: 436

```
<212> TYPE: PRT
<213> ORGANISM: Artificial Sequence
<220> FEATURE:
<223> OTHER INFORMATION: Synthetic

<400> SEQUENCE: 48

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Ile Asp Leu Gly Leu Asn
        115                 120                 125

Asn Leu Asn Thr Leu Pro Ala Ser Val Phe Asn Asn Gln Val Ser Leu
    130                 135                 140

Lys Ser Leu Asn Leu Gln Lys Asn Leu Ile Thr Ser Val Glu Lys Lys
145                 150                 155                 160

Val Phe Gly Pro Ala Phe Arg Asn Leu Thr Glu Leu Asp Met Arg Phe
                165                 170                 175

Asn Pro Phe Asp Cys Thr Cys Glu Ser Ile Ala Trp Phe Val Asn Trp
            180                 185                 190

Ile Asn Glu Thr His Thr Asn Ile Pro Glu Leu Ser Ser His Tyr Leu
        195                 200                 205

Cys Asn Thr Pro Pro His Tyr His Gly Phe Pro Val Arg Leu Phe Asp
    210                 215                 220

Thr Ser Ser Cys Lys Asp Ser Ala Pro Phe Glu Leu Phe Phe Met Ile
225                 230                 235                 240

Asn Thr Ser Ile Leu Leu Ile Phe Ile Phe Ile Val Leu Leu Ile His
                245                 250                 255

Phe Glu Gly Trp Arg Ile Ser Phe Tyr Trp Asn Val Ser Val His Arg
            260                 265                 270

Val Leu Gly Phe Lys Glu Ile Asp Arg Gln Thr Glu Gln Phe Glu Tyr
        275                 280                 285

Ala Ala Tyr Ile Ile His Ala Tyr Lys Asp Lys Asp Trp Val Trp Glu
    290                 295                 300

His Phe Ser Ser Met Glu Lys Glu Asp Gln Ser Leu Lys Phe Cys Leu
305                 310                 315                 320

Glu Glu Arg Asp Phe Glu Ala Gly Val Phe Glu Leu Glu Ala Ile Val
                325                 330                 335

Asn Ser Ile Lys Arg Ser Arg Lys Ile Ile Phe Val Ile Thr His His
            340                 345                 350

Leu Leu Lys Asp Pro Leu Cys Lys Arg Phe Lys Val His His Ala Val
        355                 360                 365

Gln Gln Ala Ile Glu Gln Asn Leu Asp Ser Ile Ile Leu Val Phe Leu
    370                 375                 380

Glu Glu Ile Pro Asp Tyr Lys Leu Asn His Ala Leu Cys Leu Arg Arg
```

-continued

```
385                 390                 395                 400

Gly Met Phe Lys Ser His Cys Ile Leu Asn Trp Pro Val Gln Lys Glu
                405                 410                 415

Arg Ile Gly Ala Phe Arg His Lys Leu Gln Val Ala Leu Gly Ser Lys
            420                 425                 430

Asn Ser Val His
        435
```

US 8,066,981 B2

COMPOSITIONS AND METHODS RELATED TO TOLL-LIKE RECEPTOR-3

FIELD OF INVENTION

The invention relates to compositions and methods related to Toll-like receptor (TLR) polypeptides. In some embodiments, the invention relates to managing TLR3 related diseases. In further embodiments, the invention relates to methods of preventing and treating inflammation. In some embodiments, the invention relates to antagonists of TLR3, to amino acid sequences that act as dominant negative molecules, and to nucleic acid sequences that encode said amino acid sequences. In additional embodiments, the invention relates to the manipulation of biological materials to evaluate TLR3 activity.

BACKGROUND OF INVENTION

Toll-like receptor 3 (TLR3) has been shown to be involved in inflammation processes. Inflammation is the body's protective response to an injury that is caused by cytokines. Overstimulation of the inflammation response is a factor in a variety of inflammatory diseases. For example, inflammation of the joints is associated with rheumatoid arthritis. Inflammation of the small tubes that transport air to the lungs is associated with asthma. Non-steroidal anti-inflammatory drugs may be used to treat these symptoms. However, these drugs often have varying success as well as adverse side effects. Thus, there is a need to identify compositions and methods for managing inflammatory responses that have limited adverse affects.

SUMMARY OF INVENTION

The invention relates to compositions and methods related to Toll-like receptor (TLR) polypeptides. In some embodiments, the invention relates to managing TLR3 related diseases. In further embodiments, the invention relates to methods of preventing and treating inflammation. In some embodiments, the invention relates to antagonists of TLR3, to amino acid sequences that act as dominant negative molecules, and to nucleic acid sequences that encode said amino acid sequences. In additional embodiments, the invention relates to the manipulation of biological materials to evaluate TLR3 activity.

In some embodiments, the invention relates to a pharmaceutical composition comprising an amino acid sequence that is a TLR3 mutant that is a dominant negative inhibitor of a TLR polypeptide. In further embodiments, said TLR is wild-type TLR3 or TLR9. In further embodiments, said TLR3 mutant is not a TIR deleted construct. In further embodiments, said TLR3 comprises C and N-terminal motifs capable of disulfide bond formation. In further embodiments, the mutant is in Loop2 within TLR3. In further embodiments, the amino acid sequence comprises the motif HANPGGIY (SEQ ID NO:41).

In some embodiments, TLR3 mutant interacts with other TLRs.

In some embodiments, the invention relates to a composition comprising a polypeptide mutant of SEQ ID NO.:1. In further embodiments, said mutant is one or more selected from the group consisting of C242A, C356A, C28A, C37A, C37S, C37M, C95A, C122A, C122S, C122M, C649A, C649S, C649M, C651A, C696A, C696S, C696M, R65A, K89A, K117A, K137A, K139A, K147A, K163A, K210A, R331A, R394A, K418A, K493A, K589A, K613A, K627A, R635A, R643A, H539E, N541A, N466A, R489A, N515A, N516A, N517A, N540A, R544A, N572A, E442A, E442D, E442K, K467A, K467E, K547A, and D575A (SEQ NO:43) In further embodiments, said mutant is a dominant negative inhibitor of a TLR. In further preferred embodiments, said mutant is a dominant negative inhibitor of wild-type TLR3 or TLR9.

In further embodiments, the invention relates to a pharmaceutical composition comprising an antibody to TLR3. In further embodiments, the antibody is to Loop2. In further embodiments, the antibody is humanized.

In additional embodiments, the invention relates to a TLR3 polypeptide comprising a tag in Loop1. In further embodiments, said tag comprises a cysteine amino acid. In further embodiments, said tag complexes with arsenic containing fluorophores.

In some embodiments, the invention relates to a pharmaceutical composition comprising an amino acid sequence with a substituted or unsubstituted motif $X^1X^2NX^4GGPX^8X^9$ wherein $X^1, X^2, X^4, X^8$, and $X^9$ are each individually and independently a naturally or nonnaturally occurring amino acid (SEQ ID NO:42). In further embodiments, $X^1$ is H, R, or N; $X^2$ is A or N; $X^4$ is P or V; $X^8$ is I or V; and $X^9$ is Y, H, Q, N, and M (SEQ ID NO:2). In further embodiments, said amino acid sequence is less than 500, 400, 300, 200, 100, 50, or 25 residues.

In additional embodiments, the invention relates to a method of preventing or treating inflammatory diseases comprising: i) providing; a) a subject diagnosed with or at risk for an inflammatory disease and b) a pharmaceutical composition comprising a dominant negative TLR3 molecule; and ii) administering said pharmaceutical composition to said subject under conditions such that said an inflammatory response is prevented or treated. In further embodiments, said inflammatory disease is selected from the group consisting of pulmonary diseases, autoimmune diseases, fibrotic diseases, and kidney diseases. In further embodiments, said pulmonary disease is selected form the group consisting of asthma, asthma exacerbation, microbial-associated pneumonia, sarcoidosis and cystic fibrosis. In further embodiments, said autoimmune disease is selected from the group consisting of rheumatoid arthritis, psoriatic arthritis, and giant cell arteritis. In further embodiments, said kidney disease is lupus nephritis. In further embodiments, said fibrotic disease is liver fibrosis. In further embodiments, said dominant negative TLR3 molecule is an amino acid sequence with the substituted or unsubstituted motif $X^1X^2NX^4GGPX^8X^9$ wherein $X^1, X^2, X^4, X^8$, and $X^9$ are each individually and independently a naturally or nonnaturally occurring amino acid (SEQ ID NO:42). In further embodiments, $X^1$ is H, R, or N; $X^2$ is A or N; $X^4$ is P or V; $X^8$ is I or V; and $X^9$ is Y, H, Q, N, and M (SEQ ID NO:2). In further embodiments, said amino acid sequence is less than 500 residues. In further embodiments, the method further comprises administering a second therapeutic agent to said subject. In further embodiments, said second therapeutic agent is selected from the group consisting of antimicrobial agents, corticosteroids and immuno-modulatory agents. In further embodiments, said antimicrobial agent is selected from the group consisting of an antibacterial agent, antiviral agents, antifungal agents, and antiparasitic agent. In further embodiments, said immuno-modulatory agent is selected from the group consisting of interferon gamma-1b, IFN-gamma, Actimmune, Tysabri, Natalizumab, Xolair, Omalizumab, Neulasta, Pegfilgrastim, Neupogen, Filgrastim, Anakinra, Humira, Adalimumab, Enbrel, TNF, Etanercept, Alefacept, Remicade, Infliximab, Raptiva, Efalizumab, Thymoglobulin, Infergen, Interferon, Muromaonab, Zenapax, Daclizumab, and Basiliximab. In further embodiments, said corticosteroid is selected from the group consisting of dexamethasone (Decadron), hydrocortisone, methylprednisolone (Medrol), prednisone, cortisone, betamethasone, and prednisolone. In further embodiments, said antibacterial agent is selected from the group consisting of sulfanilamide, Trimethoprim penicillin G, cephalexin, cefaclor, cefixime, meropenem, ertapenem, chlortetracycline, oxytetracycline erythromycin, azithromycin, and clarithromycin, clindamycin, quinupristin/dalfopristin, Ciprofloxacin Spectinomycin, Vancomycin, linezolid, and daptomycin. In further embodiments, said antiviral is selected from the group consisting of bacavir, acyclovir, agenerase, amatadine, amprenavir, crixivan, delavirdine, denavir, didanosine, efavirenz, epivir, famciclovir, famvir, fortovase, hivid, indinavir, ribavirin, invirase, lamivudine, nelfinavir, nevirapine, norvir, oseltamivir, penciclovir, relenza, rescriptor, retrovir, ritonavir, saquinavir, stavudine, sustiva, symdine, symmetrel, tamiflu, valacyclovir, valtrex, videx, viracept, viramune, zalcitabine, zerit, ziagen, zidovudine, zovirax, and zanamivir. In further embodiments, said antifungal agent is selected from the group consisting of nystatin, clotrimazole, econazole, ciclopirox olamine, ketoconazole, miconazole, terbinafine, and tolciclate. In further embodiments, said administration is selected from the group consisting of subcutaneous, oral, intravenous, intradermal, and intranasal routes.

In additional embodiments, the invention relates to a method of preventing or treating inflammatory diseases comprising: i) providing; a) a subject diagnosed with or at risk for an inflammatory disease and b) a pharmaceutical composition comprising a nucleic acid sequence that encodes a dominant negative TLR3 amino acid sequence; and ii) administering said pharmaceutical composition to said subject under conditions such that said inflammatory response is prevented or treated. In further embodiments, said inflammatory disease is selected from the group consisting of pulmonary diseases, autoimmune diseases, fibrotic diseases, and kidney diseases. In further embodiments, said pulmonary disease is selected from the group consisting of asthma, asthma exacerbation, microbial-associated pneumonia, sarcoidosis and cystic fibrosis. In further embodiments, said autoimmune disease is selected from the group consisting of rheumatoid arthritis, psoriatic arthritis, and giant cell arteritis. In further embodiments, said kidney disease is lupus nephritis. In further embodiments, said fibrotic disease is liver fibrosis. In further embodiments, said dominant negative TLR3 amino acid sequence is an amino acid sequence with the substituted or unsubstituted motif $X^1X^2NX^4GGPX^8X^9$ wherein $X^1, X^2, X^4, X^8$, and $X^9$ are each individually and independently a naturally or nonnaturally occurring amino acid (SEQ ID NO:42). In further embodiments, $X^1$ is H, R, or N; $X^2$ is A or N; $X^4$ is P or V; $X^8$ is I or V; and $X^9$ is Y, H, Q, N, and M (SEQ ID NO:2). In further embodiments, said amino acid sequence is less than 500 residues. In further embodiments, the method further comprises administering a second therapeutic agent to said subject. In further embodiments, said second therapeutic agent is selected from the group consisting of antimicrobial agents, corticosteroids and immuno-modulatory agents. In further embodiments, said antimicrobial agent is selected from the group consisting of antibacterial agents, antiviral agents, antifungal agents, and antiparasitic agents. In further embodiments, said immuno-modulatory agent is selected from the group consisting of interferon gamma-1b, IFN-gamma, Actimmune, Tysabri, Natalizumab, Xolair, omalizumab, Neulasta, Pegfilgrastim, Neupogen, Filgrastim, Anakinra, Humira, Adalimumab, Enbrel, TNF, Etanercept, Alefacept, Remicade, infliximab, Raptiva, Efalizumab, Thymoglobulin, Infergen, Interferon, Muromaonab, Zenapax, Daclizumab, and Basiliximab. In further embodiments, said corticosteroid is selected from the group consisting of dexamethasone (Decadron), hydrocortisone, methylprednisolone (Medrol), prednisone, cortisone, betamethasone, and prednisolone. In further embodiments, said antibacterial agent is selected from the group consisting of sulfanilamide, Trimethoprim penicillin G, cephalexin, cefaclor, cefixime, meropenem, ertapenem, chlortetracycline, oxytetracycline erythromycin, azithromycin, and clarithromycin, clindamycin, quinupristin and dalfopristin, Ciprofloxacin Spectinomycin, Vancomycin, linezolid, and daptomycin. In further embodiments, said antiviral agent is selected from the group consisting of bacavir, acyclovir, agenerase, amatadine, amprenavir, crixivan, delavirdine, denavir, didanosine, efavirenz, epivir, famciclovir, famvir, fortovase, hivid, indinavir, ribavirin, invirase, lamivudine, nelfinavir, nevirapine, norvir, oseltamivir, penciclovir, relenza, rescriptor, retrovir, ritonavir, saquinavir, stavudine, sustiva, symdine, symmetrel, tamiflu, valacyclovir, valtrex, videx, viracept, viramune, zalcitabine, zerit, ziagen, zidovudine, zovirax, and zanamivir. In further embodiments, said antifungal agent is selected from the group consisting of nystatin, clotrimazole, econazole, ciclopirox olamine, ketoconazole, miconazole, terbinafine, and tolciclate. In further embodiments, said administration is selected from the group consisting of subcutaneous, oral, intravenous, intradermal, and intranasal routes.

In some embodiments, the invention relates to a method of inhibiting Toll-like receptor 3 activity comprising: i) providing; a) a cell comprising TLR3 and b) a dominant negative TLR3 amino acid sequence, and ii) mixing said cell and said amino acid sequence under conditions such that TLR3 activity is inhibited. In further embodiments, said amino acid sequence is a mutant of an amino acid sequence with a substituted or unsubstituted motif $X^1X^2NX^4GGPX^8X^9$ wherein $X^1, X^2, X^4, X^8$, and $X^9$ are each individually and independently a naturally or nonnaturally occurring amino acid (SEQ ID NO:42). In further embodiments, $X^1$ is H, R, or N; $X^2$ is A or N; $X^4$ is P or V; $X^8$ is I or V; and $X^9$ is Y, H, Q, N, and M (SEQ ID NO:2). In further embodiments, said amino acid sequence is not ΔTIR. In further embodiments, said cells are selected from the group HEK, HeLa, COS, and Chinese Hamster Ovary cells.

In further embodiments, the invention relates to a method of diagnosing a TLR3 related disease comprising: a) providing; i) a subject having cells that encode TLR3 and ii) a composition comprising a nucleic acid sequence encoding a nucleic acid sequence disclosed herein; b) mixing said cells and said nucleic acid sequence under conditions such that said TLR3 activity is measured. In further embodiments, said measured activity is inhibited. In further embodiments, said cells are selected from the group consisting of lung cells, kidney cells, and synovial fibroblasts. In further embodiments, said nucleic acid sequence is wild-type TLR3 or a dominant negative inhibitor of wild-type TLR3.

In additional embodiments, the invention relates to pharmaceutical compositions comprising a non-steroidal anti-inflammatory compound and amino acid sequences disclosed herein.

In some embodiments, the invention relates use of a dominant negative inhibitor of wild-type T for the manufacture of a medicament for the management of diseases disclosed herein.

In additional embodiments, the invention relates to the use of composition disclosed herein, including mutant TLR molecules as a reagent to identify molecule inhibitors by screening for binding. In further embodiments, screening involves correlating relative binding between the wild-type TLR and mutant TLR polypeptides. In further embodiments, the mutant TLR molecule is used in a cell-based assay for modular activity for cytokine productions. In further embodiments, the mutant TLR molecule is administered to a live subject.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 1 shows a cell-based assay to detect TLR3 activity. A) Effects of increasing concentration of plasmid expressing wild-type TLR3 on the activation of luciferase reporter activity in HEK 293T cells. The luciferase activity is expressed as the ratio of the firefly luciferase driven from promoter containing NF-kB elements over the activity of the Renilla luciferase driven from the herpevirus thymidine kinase promoter. Activation of the firefly luciferase activity requires poly(I:C), added at 2.5 µg/ml of cell culture. Inset, a demonstration that HEK293 cells does not express endogenous level of TLR3. B) The TLR3 cell-based assay can detect a range of luciferase activity, from the higher levels seen with wild-type TLR3 and a mutant that has a deletion of an internal loop in TLR3.

FIG. 6 shows poly(I:C) binding by TLR3ECD in vitro. A) Crosslinking between TLR3 ECD and poly(I:C) as a function of pH. Poly(I:C) was radiolabeled by kinasing with $^{32}P$-$\gamma$-ATP and T4 polynucleotide kinase. The crosslinking was performed with an equal mixture of TLR3ECD and BSA. The phosphorimage of the crosslinked products are shown in the image on the left and the Coomassie blue-stained gel is shown in the right image. B) Effect of poly(I:C) length on RNA crosslinking as a function of pH. Poly(I:C) of 40-bp and 20-bp were radiolabeled separately and used as probes. The phosphorimage and the Coomassie Blue-stained gel images are on the left and right, respectively. C) Competition for TLR3ECD binding to poly(I:C) by competitor RNAs added to the reactions at 2-4 fold of the 20-bp poly(I:C). The RNAs used are shown above the lanes in the gel image in which the RNA was added. The effect on crosslinking to the 20-bp poly(I:C) was quantified below the gel image.

FIG. 12 shows alignment of TLR3ECD homologous sequences across a broad range of vertebrates (SEQ ID NOs: 33-40). The protein-protein interacting residues we identified are highlighted in red and RNA interaction residues in yellow.

FIG. 13 shows (SEQ ID NOs: 1) which is *homo sapiens* TLR3.

DETAILED DESCRIPTION OF INVENTION

Figure 2C:
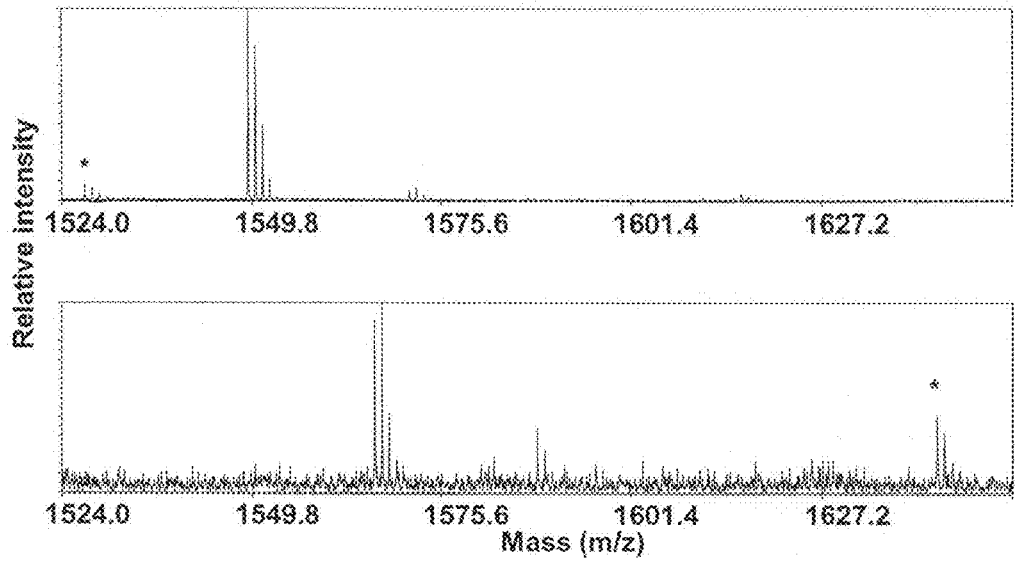
FIG. 2 shows detection of disulfide bonds in the 3ECD. A) A 3ECD structure (PDB id 2A0Z) showing the residues near the N- and C-terminal portions of the 3ECD, which participate in disulfide bond formation. B) Sequence analysis of the cysteines in TLR3ECDs from species across a wide phylogenetic range (SEQ ID NOs:4-17). The cysteine pairs involved in disulfide bond formation are indicated by the brackets. C) Mass spectra of a tryptic digest of TLR3 protein focusing on the m/z region containing the CTVSHEVADCSHLK (SEQ ID NO:3) peptide. The top spectrum is of the peptide containing the disulfide bond. The bottom spectrum is the reduced and alkylated form of the peptide. D) Tandem mass spectrometry analysis of the above peptide to confirm the assigned peptide sequence.

The invention relates to compositions and methods related to toll-like receptor (TLR) polypeptides. In some embodiments, the invention relates to managing and diagnosing TLR3 related diseases. In further embodiments, the invention relates to methods of preventing and treating inflammation. In some embodiments, the invention relates to antagonists of TLR3, to amino acid sequences that act as dominant negative molecules, and to nucleic acid sequences that encode said amino acid sequences. In additional embodiments, the invention relates to the manipulation of biological materials to evaluate TLR3 activity.

Toll-like receptors (TLRs) are type I transmembrane proteins that often recognize microbes once they have breached physical barriers such as the skin or intestinal tract mucosa, and activate immune cell responses. Thirteen TLRs (named simply TLR1 to TLR13) have been identified in humans and mice together, and equivalent forms of many of these have been found in other mammalian species.

A dominant negative mutation occurs when a mutant gene product affects the normal, wild-type gene product within the same cell. This usually occurs if the product of the mutation can still interact with the same elements as the wild-type product, but block some aspect of its function. The term "dominant negative inhibitor" and the like means a mutant gene product of a dominant negative mutation. As used herein, it is not intended to be limited in the manner in which the dominant negative inhibitor is made, and some embodiments contemplate that it is produced synthetically. It is also intended to include the mutant gene product that provides partial inhibition or function alteration, and it is not intended to require total inhibition.

The term "manage" when used in connection with a disease or condition means to provide beneficial effects to a patient being administered with a prophylactic or therapeutic agent, which does not result in a cure of the disease. In certain embodiments, a patient is administered with one or more prophylactic or therapeutic agents to manage a disease so as to prevent the progression or worsening of the disease.

As used herein, the terms "prevent" and "preventing" include the prevention of the recurrence, spread or onset. It is not intended that the present invention be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, the present invention also contemplates treatment that merely reduces symptoms, and/or delays disease progression.

"Inflammation" or "inflammatory response" and the like means reaction of the body to injury or to infectious agent, allergic agent, abnormality in the regulation of the body's immune response to its own tissues, non-living foreign material, or a chemical irritation. The symptoms are redness, swelling, heat, and pain resulting from dilation of the blood vessels in the affected part with loss of plasma and leucocytes (white blood cells) into the tissues. Inflammation can be acute or chronic. Inflammatory responses include, but are not limited to, those attributable to tuberculosis, chronic cholecystitis, bronchiectasis, rheumatoid arthritis, Hashimoto's thyroiditis, inflammatory bowel disease (ulcerative colitis and Crohn's disease), silicosis and other pneumoconiosis, asthma, multiple sclerosis, hepatitis, chronic obstructive pulmonary disease, hay fever and other allergies, cardiovascular disease, implanted foreign body, systemic lupus erythematosus, and type 1 diabetes.

"Subject" means any animal, preferably a human patient, livestock, or domestic pet.

Some embodiments of the present invention provide mutant or variant forms of enzymes described herein. It is possible to modify the structure of a peptide having an activity of the enzymes described herein for such purposes as enhancing substrate specificity, stability, and the like. For example, a modified peptide can be produced in which the amino acid sequence has been altered, such as by amino acid substitution, deletion, or addition. For example, it is contemplated that an isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Accordingly, some embodiments of the present invention provide variants of enzymes described herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer (ed.), *Biochemistry*, 2nd ed, W H Freeman and Co. [1981]). Whether a change in the amino acid sequence of a peptide results in a functional homolog can be readily determined by assessing the ability of the variant peptide to produce a response in a fashion similar to the wild-type protein using the assays described herein. Peptides in which more than one replacement has taken place can readily be tested in the same manner.

The term "antibody", as used herein, refers to a molecule specifically binding to an antigen, and includes dimeric, trimeric and multimeric antibodies, and recombinant, processed and humanized antibodies. Also, an antibody may be a whole antibody or a functional fragment of an antibody molecule. The term "functional fragment of an antibody molecule" indicates a fragment retaining at least its antigen binding function, and include Fab, F(ab'), F(ab')$_2$, scFv, dsFv, and diabody. Techniques for the preparation and use of the various antibodies are well known in the art. For example, antibody fragments may be obtained using proteolytic enzymes (e.g., a whole antibody is digested with papain to produce Fab fragments, and pepsin treatment results in the production of F(ab')$_2$ fragments), and may be preferably prepared by recombinant DNA techniques. An isolated antibody any collected composition containing the antibody. Preferably the concentration of said antibody is greater than that found in blood serum.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody may also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference).

Importantly, early methods for humanizing antibodies often resulted in antibodies with lower affinity than the non-human antibody starting material. More recent approaches to humanizing antibodies address this problem by making changes to the CDRs. See U.S. Patent Application Publication No. 20040162413, hereby incorporated by reference. In some embodiments, the present invention provides an optimized heteromeric variable region (e.g. that may or may not be part of a full antibody other molecule) having equal or higher antigen binding affinity than a donor heteromeric variable region, wherein the donor heteromeric variable region comprises three light chain donor CDRs, and wherein the optimized heteromeric variable region comprises: a) a light chain altered variable region comprising; i) four unvaried human germline light chain framework regions, and ii) three light chain altered variable region CDRs, wherein at least one of the three light chain altered variable region CDRs is a light chain donor CDR variant, and wherein the light chain donor CDR variant comprises a different amino acid at only one, two, three or four positions compared to one of the three light chain donor CDRs (e.g. the at least one light chain donor CDR variant is identical to one of the light chain donor CDRs except for one, two, three or four amino acid differences).

In some embodiments, the invention relates to amino acid residues in human TLR3 found to have bioactivity. Specifically, we discovered that mutations of residues 547-554 abolished TLR3 bioactivity as measured by NF-KB activation. Moreover, co-transfection of competent human Hek293 cells with bioactive and mutant human TLR3 genes resulted in loss of TLR3 activity, demonstrating the ability of the mutant TLR3 molecule to act as a dominant negative molecule. The antagonistic activity of the TLR3 mutant molecules provide a unique tool to interfere with TLR3 activity, which proves beneficial in preventing and treating TLR3-mediated diseases including inflammation. We have also identified that a mutant TLR3 interacts with other TLRs including TLR9.

TLR3 activation by ligands derived from viral RNA, bacterial RNA or endogenous necrotic cells results in a signaling cascade that ultimately leads to NF-kB activation and downstream secretion of pro-inflammatory cytokines and chemokines including IL-6, RANTES, TNF-$\alpha$, MCP-1 to cite a few. It is well established from experiments performed in animal models that inflammatory cytokines and chemokines play a critical role in initiating and maintaining the local inflammatory response and subsequent tissue destruction. Therefore antagonist TLR3 agents such as dominant negative TLR3 molecules is beneficial in preventing or treating inflammatory conditions.

Activation of TLR3 in the lungs has been suggested to mediate exacerbation of the local inflammatory response. Thus, the use of dominant negative TLR3 molecules described herein can prove beneficial for the treatment or prevention of pulmonary diseases including asthma, asthma exacerbation, microbial-associated pneumonia, sarcoidosis and cystic fibrosis.

The presence of necrotic cells in the synovial fluid of rheumatoid arthritis patients has been shown to activate TLR3 and downstream secretion of inflammatory mediators, suggesting a role for TLR3 activation in modulating disease outcome in rheumatoid arthritis patients. Therefore, the dominant negative TLR3 molecules are beneficial for the treatment of autoimmune diseases including RA, psoriatic arthritis, and giant cell arteritis.

TLR3 activation in the liver is an important event in mediating liver damage. Thus the use of TLR3 antagonist molecule such as dominant negative TLR3 molecules may alleviate liver damage and may be used for the prevention of treatment of liver damage including liver fibrosis.

The dominant negative TLR3 molecule may be used in treating autoimmune diseases such as systemic lupus erythematosus and lupus nephritis given the association between TLR3 activation in the kidney and disease activity in animal models of lupus nephritis.

The TLR3 dominant negative molecule may be used for the treatment of fibrotic-associated diseases based on recent findings showing cells derived from fibrosis-proned animals were highly susceptible to TLR3 ligands as measured by enhanced production of inflammatory cytokines such as TNF-α.

In some embodiments, the invention relates to the use of DNA encoding for dominant negative of human TLR3 molecule described herein in combination with standard therapies including antimicrobial agents, corticosteroids and immuno-modulatory agents is also claimed for the treatment or prevention of diseases described herein.

In further embodiments, the invention relates to the use of polypeptide molecules described herein for the treatment or prevention of the diseases described above.

In other embodiments, the invention relates to administration of the dominant negative molecules by using subcutaneous, oral, intravenous intradermal or intranasal routes for the treatment of diseases described above.

Toll-Like Receptor 3 (TLR3) Mutants and Sequences

The structure of the human TLR3 ectodomain (ECD) was solved by X-ray crystallography, leading to a number of models concerning TLR3 function. (Choe, J., Kelker, M. S., and Wilson, I. A. (2005). *Science* 309, 581-585 and Bell, J. K., Botos, I., Hall, P. R., Askins, J., Shiloach, J., Segal, D. M., and Davies, D. R. (2005) *Proc Natl Acad Sci USA* 102, 10976-10980). The structure revealed four pairs of cysteines that are putatively involved in disulfide bond formation. There are two loops that protrude from the central solenoid structure of the protein. We examined the recombinant TLR3 ECD for disulfide bond formation, poly(I:C) binding, and protein-protein interaction. We also made over 80 mutations in the residues that could affect these features in the full-length TLR3 and they were examined for effects in TLR3-mediated NF-KB activation. A number of mutations that affected TLR3 activity also affected the ability to act as dominant negative inhibitors of wild-type TLR3. Loss of putative RNA binding did not necessarily affect dominant negative activity. All of the results support a model where a dimer of TLR3 is the form that binds RNA and activates signal transduction.

The recognition of foreign molecules by the innate immune receptors can lead to the activation of a signaling cascade, changes in gene expression, and production of cytokines by effector cells. The consequence of this pathway dictates the outcome of an immune response through modulation of T- and B-lymphocyte activation in the adaptive immune pathways.

At least eleven TLRs have been identified in the human genome. TLR3 recognizes poly(I:C), a synthetic double-stranded (ds) RNA analog, as well as viral dsRNA, presumably formed during viral infection. A TLR3 knockout mice is unable to mount a full response to cytomegalovirus infection and decreased the cytotoxic T cell response after the initial infection in mice. These results support a role for TLR3 in modulating the host immune response against microbial challenge.

Upon ligand binding, TLR3 can, through adaptor proteins, activate the transcription factor NF-KB, which translocates to the nucleus to modulate gene expression. The site of action for TLR3 activation is likely in or near intracellular vesicles, although some cell-surface expression is observed in human embryonic kidney cells.

The structures of the TLR3 ectodomain have been elucidated by X-ray crystallography by two groups, leading to several predictions about how the structure affects function. The TLR3 ECD is shaped as a solenoid horseshoe, characteristic of proteins with multiple leucine-rich repeats (LRRs). A number of features in the protein structure could impact TLR3 function. Based on surface charge properties and the location of glycosylations, the region proposed to bind dsRNA was proposed to be free of glycosylation. The structures from the crystal packing suggest that the C-terminal portions of two subunits interact through ionic interactions. TLR3 ECD is also predicted to contain four disulfide bonds near the N- and C-termini of the solenoid that may stabilize the ECD structure. Lastly, there are two protruding loops in the 3ECD solenoid that may contribute to TLR3 function.

Analysis of how the structural features of the 3ECD impact function is an active area of research. All of the predicted N-linked glycosylation sites in TLR3 ECD have been mutated and two have been shown to be important for TLR3 activity in transfected HEK 293T cells. Several of the cysteines putatively involved in disulfide bond formation have been mutated. Bell et al., (2005) *Proc Natl Acad Sci USA* 102, 10976-10980, examined the effects of many mutations throughout the 3ECD of TLR3 and demonstrated that two residues, H539E and N541A are affected for activity in cultured 293T cells and prevented recombinant 3ECD from binding to dsRNA in a gel-filtration based assay. A thorough mutational analysis of residues neighboring H539E and N541A had more modest effects on TLR3 activity.

We have made over eighty mutants in TLR3 that are predicted to affect disulfide bond formation, dimerization, and RNA binding and examined their effects in a cell-based assay for TLR3 activation of downstream reporter expression. Biochemical assays for the properties of the TLR3 ECD produced in human cells are also examined. The effects of select mutants that decreased TLR3 activity were examined for effects on protein expression, cellular localization, and for the ability to act as dominant negatives of co-transfected wild-type copy of TLR3.

NF-kB activation assay provided for TLR3 function. Human embryonic kidney (HEK) 293T cells were used to analyze how mutations in TLR3 will affect TLR3 function and localization. 293T cells are useful for this assay since they do not express detectable levels of endogenous TLR3 (FIG. 1A, box). Briefly, cells cultured in 96-well plates to ~80% confluence were transfected with a mixture of three plasmids: one to express either wild-type or mutant TLR3, a second to express the firefly luciferase driven from promoter containing NF-kB binding sites, and a third to express the Renilla luciferase from the Herpesvirus thymidine kinase promoter. The Renilla luciferase serves as a transfection control. Poly (I:C) purchased from Invivogen was used as the ligand to induce TLR3-mediated NF-KB activation.

Our assay can respond to up to 75 ng of the TLR3 plasmid in the transfection (FIG. 1A), but our standard assay uses 15 ng of plasmid per transfection to ensure that the signal will not be saturated. The ratio of firefly luciferase to Renilla luciferase activity was calculated for all the samples induced with poly(I:C) as well as with the buffer alone control. The fold of poly(I:C) induced TLR3 activation was the normalized to the wild-type control (100%) assayed in the same experiment. A minimum of four-fold induction of TLR3 activity by the addition of poly(I:C) was detected in all of our assays (FIG. 1B). As an example, a mutant TLR3 can reduce activity to background (FIG. 1B).

Cysteines are involved in disulfide bond formation. Cysteines that putatively form disulfide bonds to cap the ends of the ECD are: C28 and C37, C95 and C122, C649 and C677, and C651 and C696 (FIG. 2A; 1, 2). The cysteines are conserved in all species in which the TLR3 orthologs have been identified ((SEQ ID NOs: 4-17), suggesting that the disulfide bonds they form are important for TLR3 function (FIG. 2B).

Figure 2D:
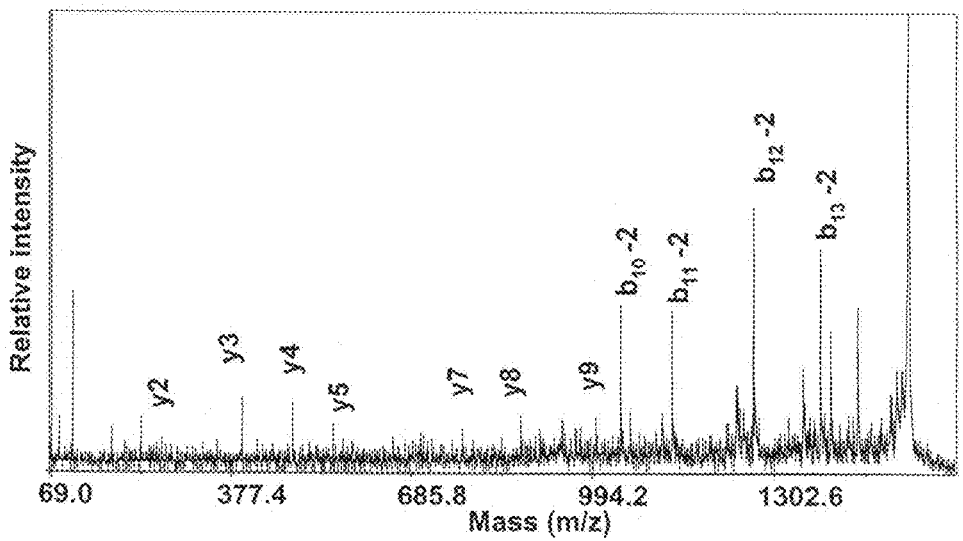

We first attempted to determine whether the formation of the disulfides could be detected in tryptically digested fragments of TLR3ECD using mass spectrometry (FIG. 2C). Reduced cysteines are acetylated by iodoacetamide and the ones involved in disulfide bond formation are not. The MS spectra obtained in the non-reduced tryptic digest resulted in a signal at 1526.81 m/z, which corresponds to the modified peptide CTVSHEVADCSHLK ((SEQ ID NOs: 3) if a disulfide was originally present (FIG. 2C top panel). To confirm the sequence and structural assignment of this peptide, tandem MS was performed (FIG. 2D). Nearly the entire C-terminal y ion series (y2 to y9) was observed, confirming the peptide sequence assignment. More significant is the observation of the b series ions b10-b13, were all 2 Da lower than what would be expected for the reduced peptide. These results confirm the presence of a disulfide bond between Cys28 and Cys37. The other three pairs of disulfides were not observed despite repeated attempts, suggesting that they may either be present at lower abundances or that the peptides containing these disulfides could not be ionized under the conditions used.

To assess the functional relevance of the disulfide bonds, we mutated each participating cysteine to alanine. Mutants C28A, C37A, C95A, C122A, C649A, C651A, and C696A all resulted in TLR3 activities near background (FIG. 3A). We also examined whether replacements of some of the cysteines with serine or methionines would affect activity. All of the changes in residues C37, C95, C122, C649, C651, and C696 resulted in activities at or near the background level. Therefore, the cysteines involved in disulfide bond formation are important for TLR3 function. In contrast, mutations of cysteine residues that are not predicted to participate in disulfide bond formation (C242, or C356, or both) had only minimal effects on TLR3 activity (FIG. 3A).

Mutations in the disulfide-forming cysteines could affect several properties of TLR3, including its expression, stability, and/or intracellular localization. To examine whether TLR3 expression was affected, lysates from transfected cells were subjected to western blots with a TLR3-specific monoclonal antibody. All cysteine mutants were expressed at levels comparable to WT (FIG. 3B). To examine whether the mutant proteins are affected in the intracellular localization of TLR3, we immunostained transfected HEK 293T cells for TLR3 and confirmed that TLR3 localizes to intracellular acidic organelles in a punctate distribution. The spots co-localized with acidic vesicles that can be stained with LysoTracker. Mutant C242A, which is not implicated in disulfide bond formation and suffered no significant loss of activity in the cell-based assay, has an appearance similar to wt TLR3 (FIG. 3C). Among the mutants involved in disulfide bond formation, C651A and C696A had suffered no obvious changes to wild-type TLR3 localization while C37A and C122A had more diffused signals rather than discrete spots (FIG. 3C). A brighter signal was also seen throughout the cytoplasm, suggesting some loss of localization to intracellular vesicles.

Figure 3D:
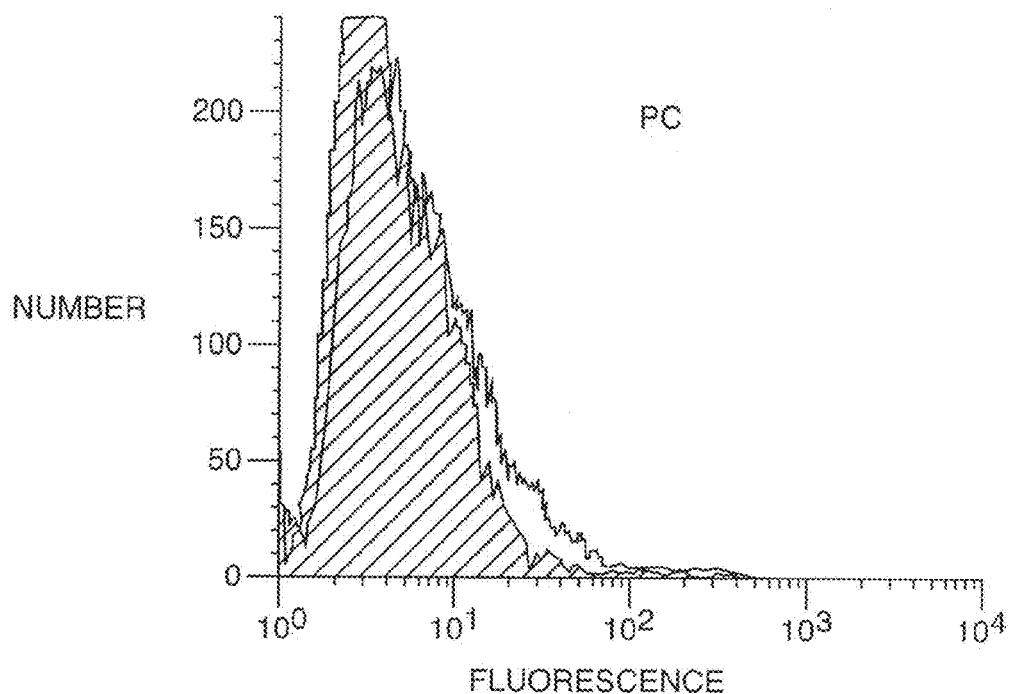
FIG. 3 shows the effects of the mutations in the cysteines involved in the disulfide bond formation. A) A summary of the effects of mutations on TLR3 activity. All mutant names contain the amino acid, their position in TLR3 and the residue to which they were mutated. All activities are normalized to the wild-type TLR3 assayed in the same experiment. B) Western blot analysis of select mutants to analyze whether the mutation affects the expression of the protein. pcDNA is the plasmid vector used to express TLR3 or mutant TLR3s. C) In situ localization of TLR3 stained with FITC-labeled monoclonal antibody specific for TLR3. The names of the samples are shown on the left, the types of image taken are shown above the micrographs. D-H) The results of FACS analysis of controls and several cysteine mutants are shown (looking at the cell-surface fluorescence). The monoclonal antibody recognizing TLR3, TLR3.7, is from eBioSciences Inc. (San Diego, Calif.). The distribution of the cells with the fluorescence intensity denoted on the horizontal axis is graphed. The shaded regions are signals from an immunoglobulin isotype of the monoclonal antibody recognizing TLR3. 'pc' corresponds to pcDNA and 'WT' to wild-type TLR3.
Figure 3E:
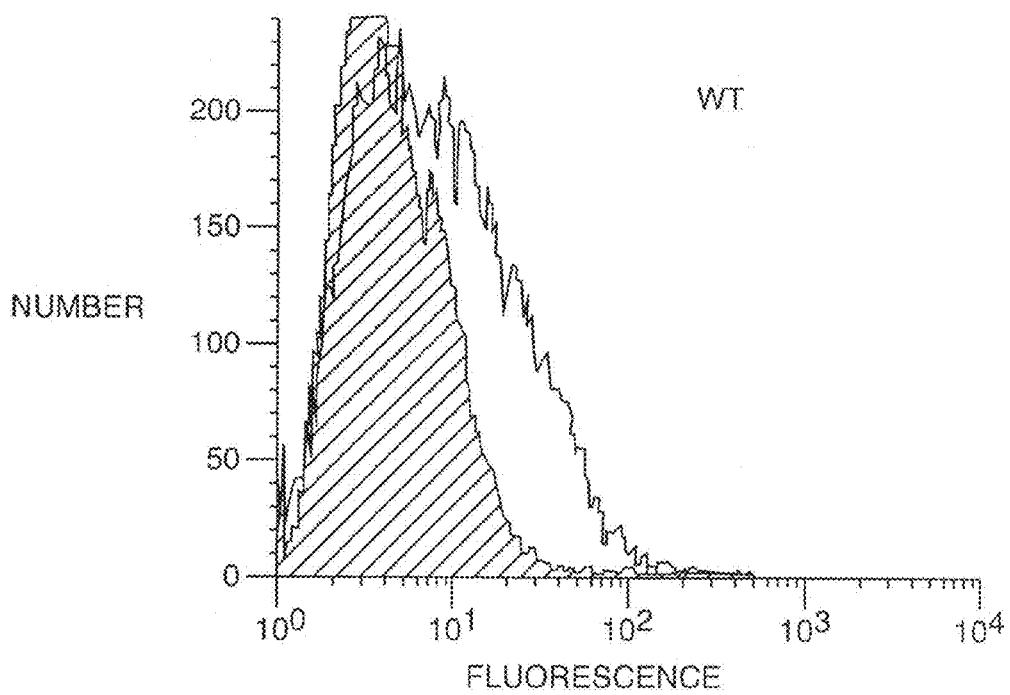
Figure 3F:
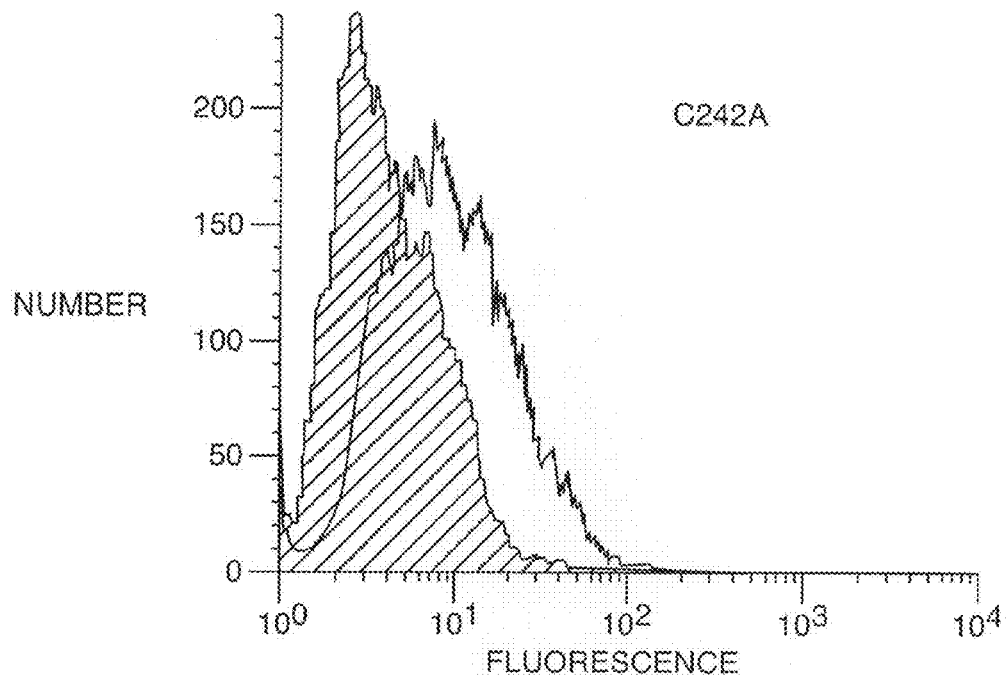
Figure 3G:
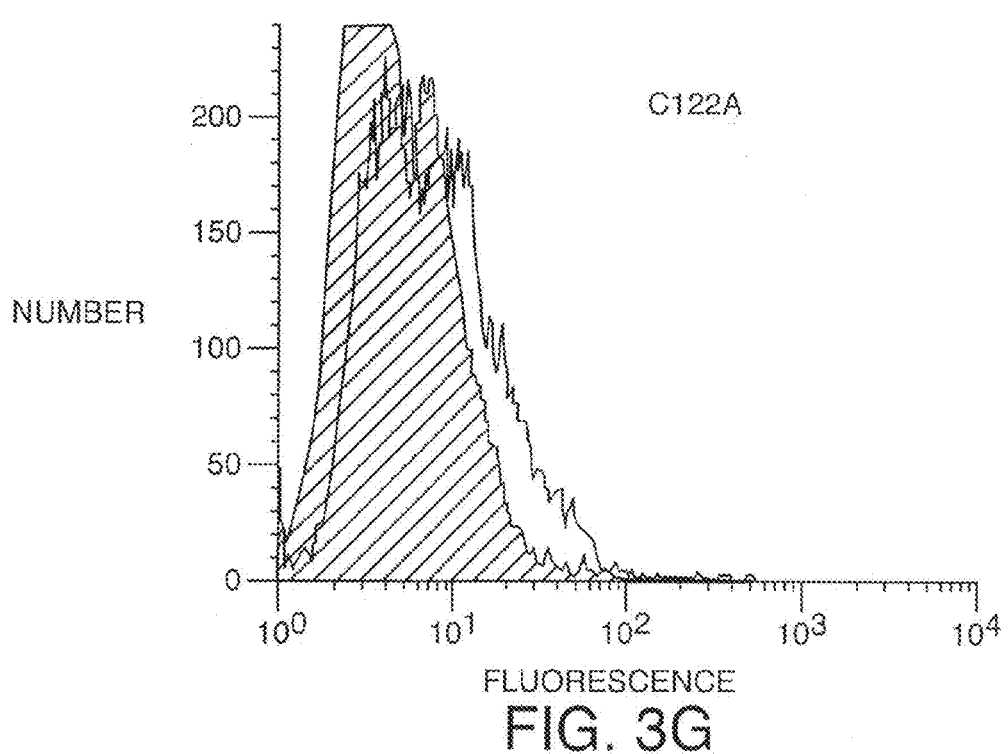
Figure 3H:
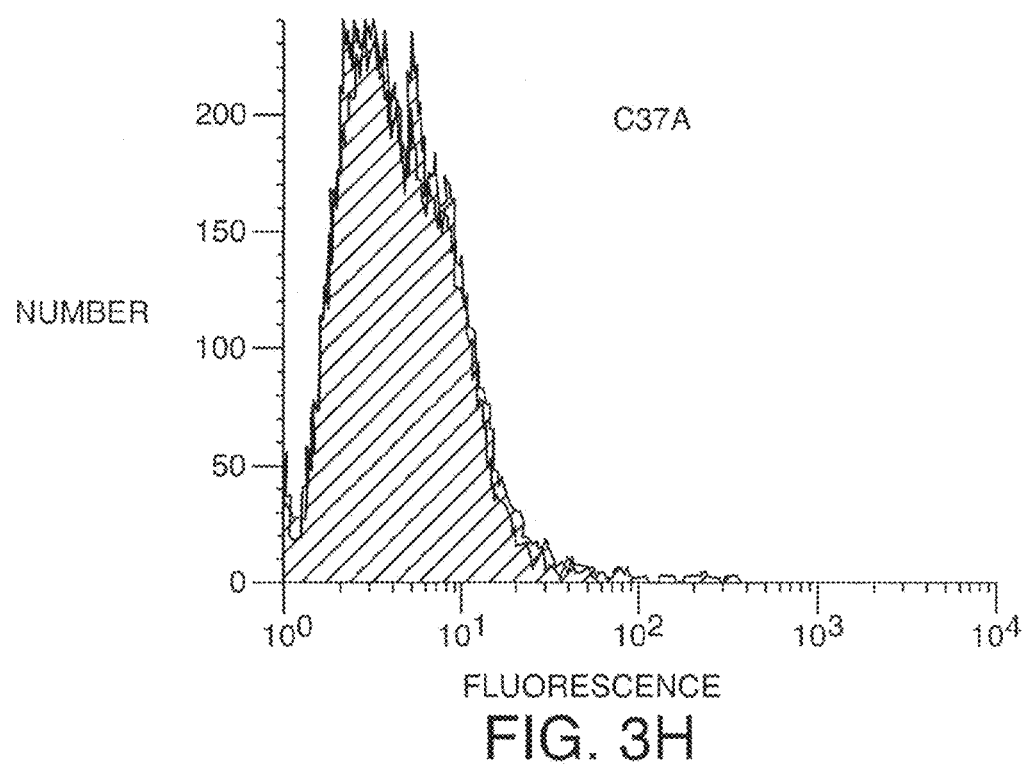

We also examined the cell surface distribution for mutants C37A and C122A by fluorescence activated cell sorting. C37A and C122A are reduced for cell surface expression (FIG. 3D). This data suggests that cysteines involved in disulfide bonds formation in TLR3 are important for activity and the mutants are expressed at levels comparable to WT, but some are affected in their intracellular localization. This change in localization contributes to the loss of TLR3 activity.

Figure 4A:
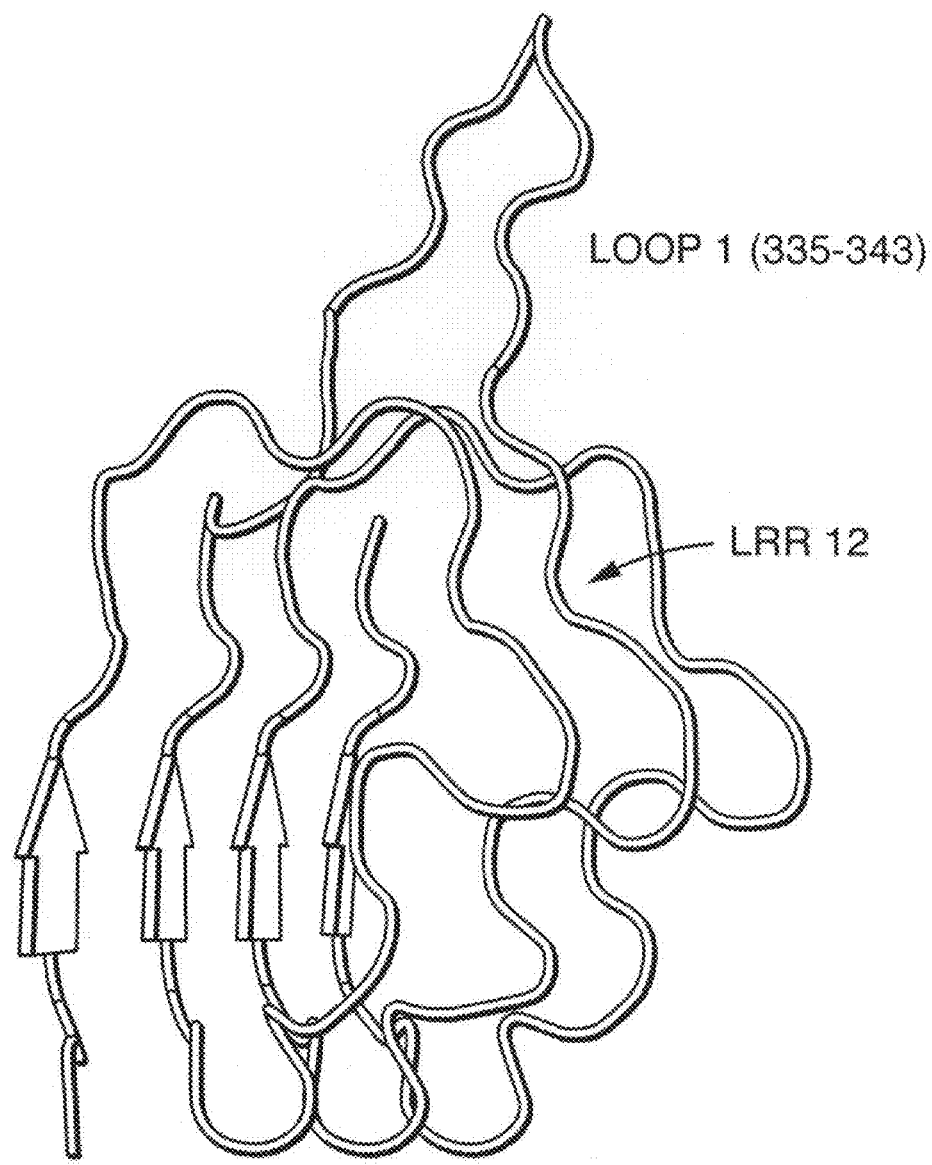
FIG. 4 shows data in examination of the role of Loop1 on TLR3 function. A) A partial model of TLR3 showing the relative location of Loop1. B) A comparison of the sequences in Loop1 from different species (SEQ ID NOs: 18-24). The residues that are different from the human Loop1 sequence are shown in bold. The residues that are apparently deleted are shown as a dash. C) Activity assay of wild-type TLR3 and mutations in Loop1 of TLR3. D) Western blot analysis examining whether the mutations in Loop1 affect protein expression. E) In situ localization of the mutant deleted for Loop1 in comparison to WT. The presence of TLR3 in punctate spots, the nuclei, and merging of the two results are shown as identified above the micrographs. The bar in the lower micrograph represents 20 µm.

Structures that project out from the central solenoid structure of TLR3 ECD could provide features important for TLR3 function. A loop within the LRRs of TLR9 has been hypothesized to interact with the ligand, CpG DNA. Bell, et al., (2003). *Trends Immunol.* 24, 528-533. TLR3 has two loops in the ECD solenoid. The first, called Loop1, resides in LRR12 (residues 335-343) and is rich in serine residues (FIGS. 4A and B). An examination of the sequence of Loop1 revealed that it is variable in its sequence and length (SEQ ID NOs: 18-24). For example, while the mammalian Loop1 is composed of eight residues ((SEQ ID NOs: 18-22), the equivalents from fish have only six residues (SEQ ID NOs: 23-24) (FIG. 4B).

Figure 4E:
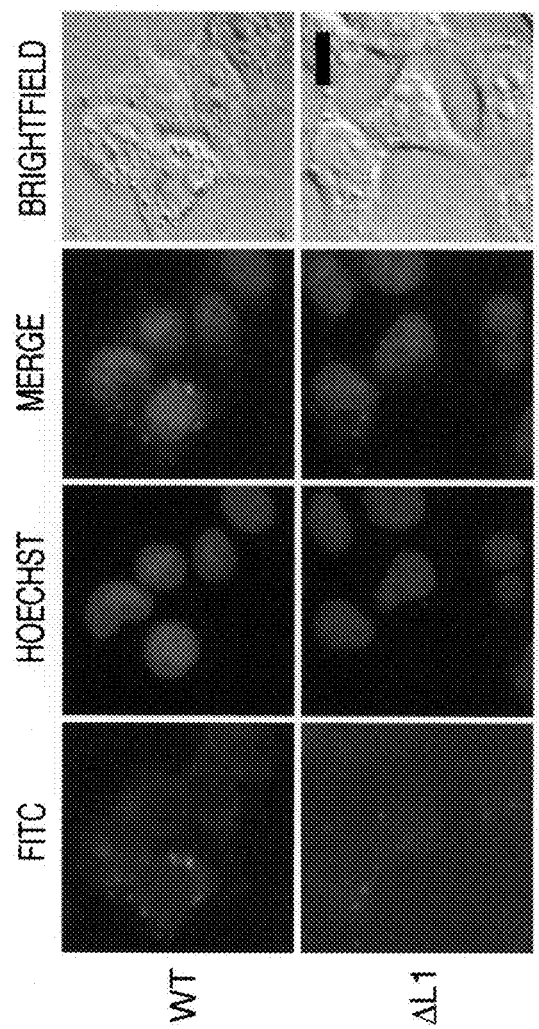
Figure 4D:
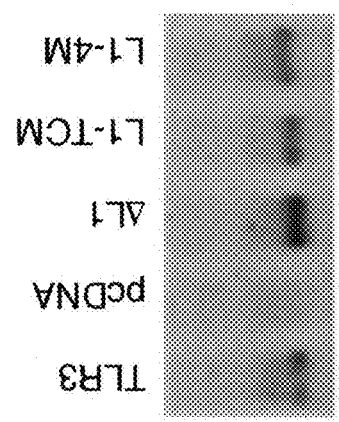

We first replaced the central six residues of Loop1 (SISLAS) (SEQ ID NOs: 44) with the six-residue sequence: CCPGCC (SEQ ID NO: 45) that could bind the FlAsH dye. See e.g, Griffin et al., (1998). *Science* 281, 269-272. Our intention was to fluorescently label TLR3 by its binding to the FlAsH dye. However, this construct, L1-TCM, did not bind the FlAsH dye well, perhaps due to steric constraints. Nonetheless, the construct was as active as the WT for NF-κB reporter activity (FIG. 4C). Next, we changed four of the residues in TLR3Loop1 from QSISLASL (SEQ ID NO:46) to QSTALTSH (SEQ ID NO:47) in a construct named L1-4M. Again, more than 85% of the TLR3 activity was retained. Lastly, we deleted Loop1 altogether (ΔL1) and found the resultant construct to retain greater than 80% of the wild-type TLR3 activity (FIG. 4C). Western analysis showed that the proteins were made similar to WT (FIG. 4D). In localization experiments, ΔL1 formed intracellular specks in a manner indistinguishable from WT (FIG. 4E). These results demonstrate that Loop1 is not essential for TLR3 function.

Figure 5A:
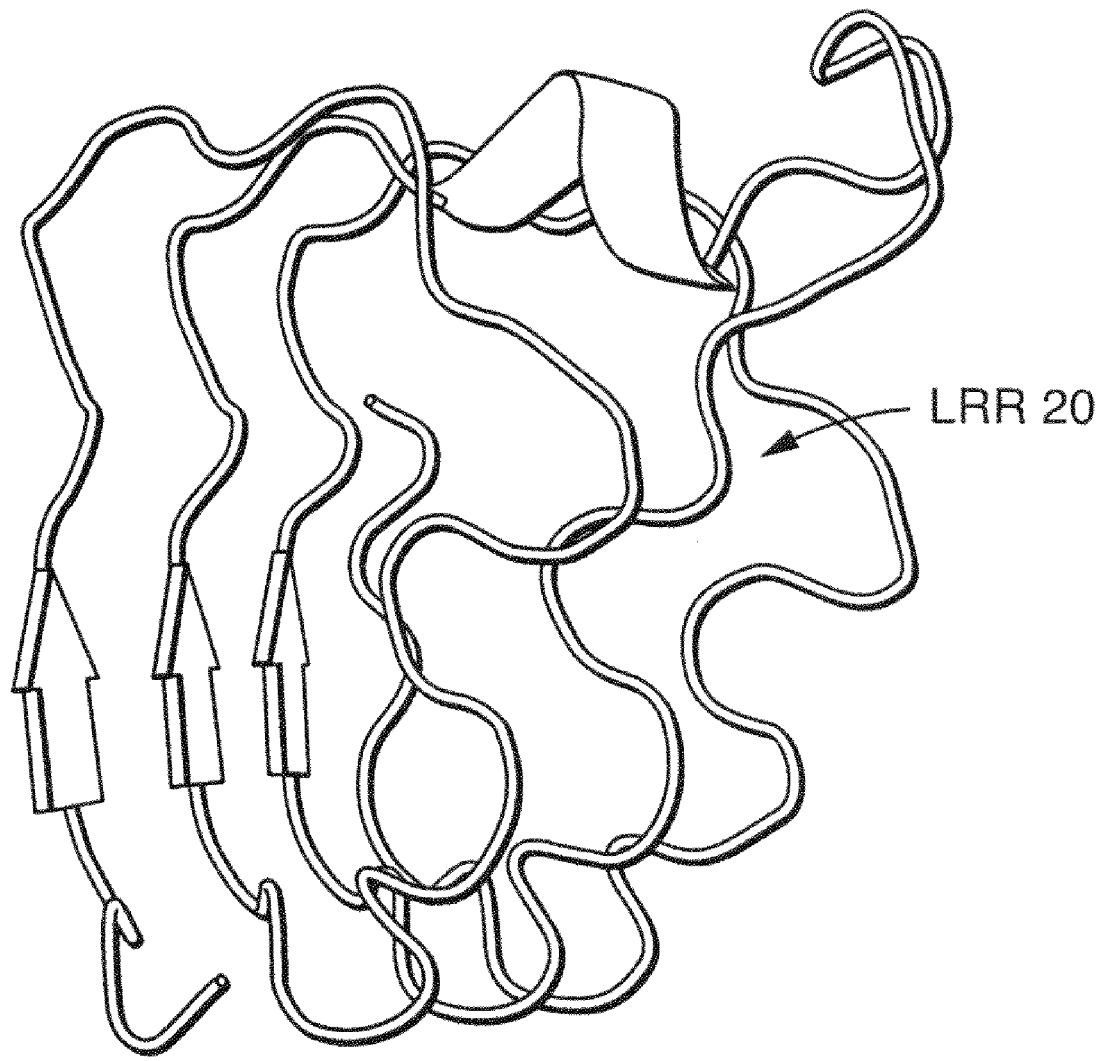
FIG. 5 shows data in examination of the role of Loop2 on TLR3 function. A) A model of a section of TLR3 showing the location of Loop2. B) A comparison of the sequences in Loop2 from different species (SEQ ID NOs: 25-32). The residues that are different from the human Loop2 sequence are shown in black. C) Activity assay of wild-type TLR3 and mutations in Loop2 of TLR3. D) Western blot analysis examining whether the mutations in Loop2 affect protein expression. E) In situ localization of the mutant deleted for Loop2 in comparison to wild-type TLR3. The presence of TLR3 in punctate spots, the nuclei, and merging of the two results are shown as identified above the micrographs. The bar in the lower micrograph represents 20 µm.
Figure 5E:
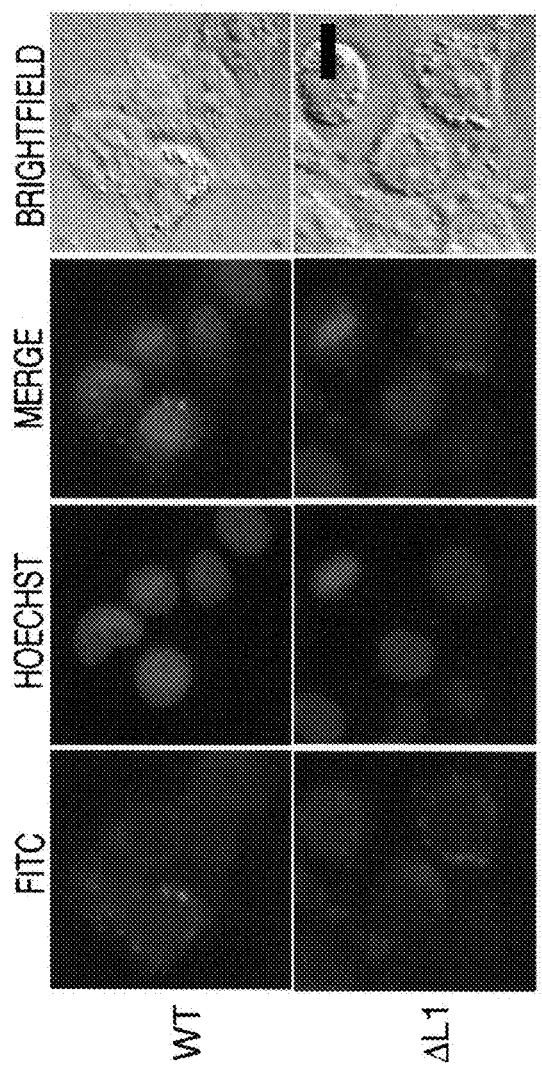
Figure 5D:
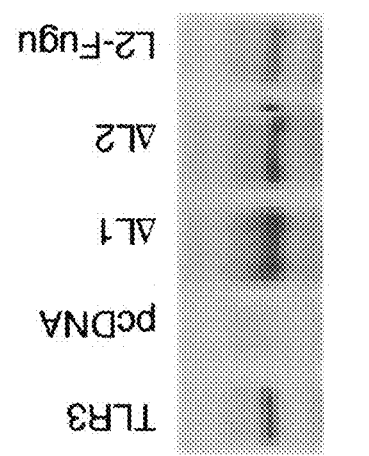

The second loop in TLR3 ECD resides within LRR20 (residues 547 to 554) (FIG. 5A). Unlike Loop1, several residues are highly conserved (FIG. 5B) (SEQ ID NOs:25-32). When the tetracysteine motif was inserted into the apex of Loop2, construct L2-TCM resulted in a protein that retained 82% of the activity of the WT (FIG. 5C). Replacement of the Loop2 sequence in TLR3 with the comparable sequence from Takifugu in construct L2-Fugu retained 75% of the wild-type function, confirming that there is some flexibility of the Loop2 sequence. However, a deletion of Loop2 in construct ΔL2 resulted in activity near background (FIG. 5C). ΔL2 protein was expressed at wild-type levels, when detected in western blots, suggesting that protein expression is not responsible for the defect (FIG. 5D). Furthermore, ΔL2 is apparently expressed as punctate spots similar to WT, indicating that different intracellular localization is not a cause of the defect (FIG. 5E).

Poly(I:C) binds the TLR3 ECD. TLR3 responds to dsRNA that could be generated during viral infection. dsRNA binding could occur either directly or through an accessory protein, such as CD14. Assays for dsRNA binding by the TLR3 ECD are limited. Choe et al., (2005) *Science* 309, 581-585, demonstrated an electrophoretic mobility shift of TLR3 ECD upon poly(I:C) binding, while Bell et al. observed a complex between the TLR3 ECD and RNA in a gel-filtration assay. We used a UV crosslinking assay to examine TLR3ECD interaction with poly(I:C) radiolabeled at the 5' terminus. Since TLR3 is localized to acidic vesicles, we also assessed whether the pH of the reaction would affect TLR3 interaction with poly(I:C). BSA was added to TLR3ECD at an equal molar ratio to provide an internal control. The TLR3ECD was crosslinked to poly(I:C) while BSA was not. We note that the poly(I:C) used in these assays are capable of inducing TLR3 activation of NF-κ,β activity. Furthermore, crosslinking to poly(I:C) was most effective at acidic pH (FIG. 6A).

Since commercial preparations of poly(I:C) is heterogeneous in mass, we prepared poly(I:C) of 40 and 20 bp for the crosslinking assay. Both were crosslinked to TLR3ECD (FIG. 6B). Lastly, to determine whether TLR3ECD specifically recognized poly(I:C), we examined whether crosslinking to the radiolabeled 20-bp poly(I:C) could be competed with other potential ligands. Competing ligands used were unlabeled poly(I:C) of 20- or 40-bp, two siRNAs of 21 bp, a highly structured RNA of 13-nt (Kim et al., 2000, *Nat Struct Biol.* 7, 415-423), and a 33-nt single-stranded unmodified RNA named—21/13 (Siegel et al., (1997). *Proc Natl Acad Sci USA* 94, 11238-11243.). The two preparations of poly(I:C) were effective competitors when present at 2-4 fold above the labeled ligand, reducing the radiolabeled complex to less than 40% of the reaction lacking a competitor (FIG. 6C). The two siRNAs, were weaker competitors, reducing poly(I:C) crosslinking to approximately a third. The structured and single-stranded RNA were the worst competitors. These results provide biochemical evidence that hTLR3ECD could specifically recognize poly(I:C) in the absence of accessory proteins.

Figure 7C:
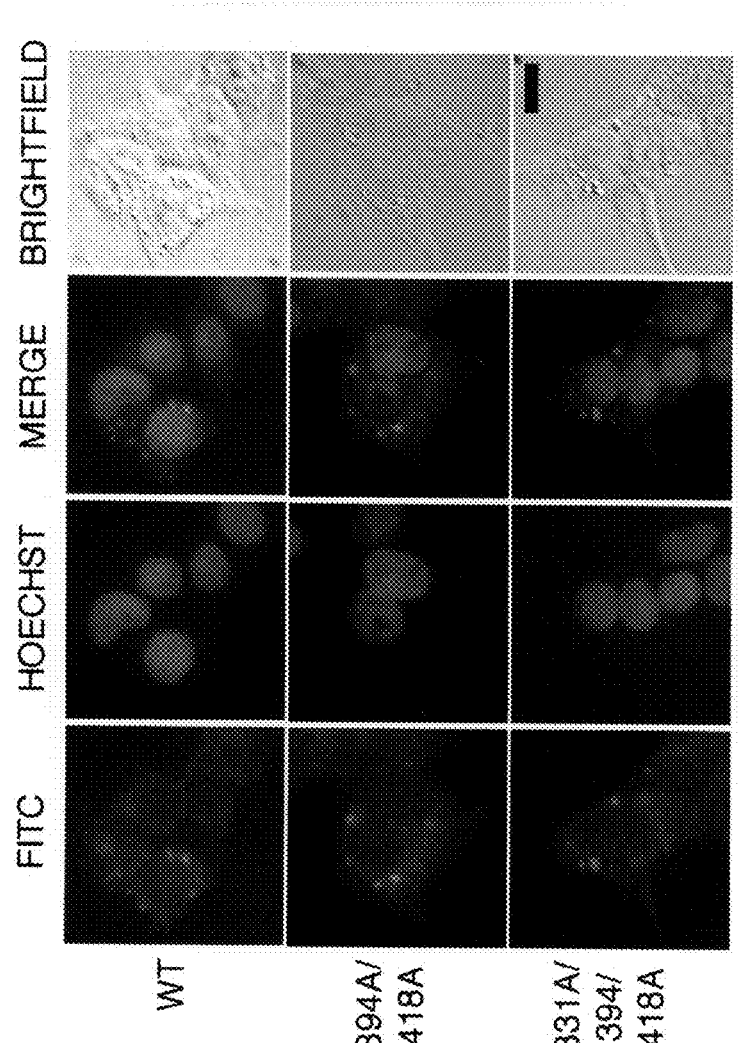
FIG. 7 show data in examination of putative RNA binding residues in TLR3ECD. A) Summary of the effects of amino acid substitutions on TLR3 activity. The plasmids encoding wild-type or mutant TLR3 that were transfected into 293T cells are listed along with their effects on luciferase activity. Each value represents a minimum of six independent transfection assays. B) Western blot analysis of some of the mutant TLR3 proteins tested for activity in the cell-based reporter assay. C) Analysis of specific TLR3 mutants for intracellular locations in transfected 293T cells.
Figure 7B:
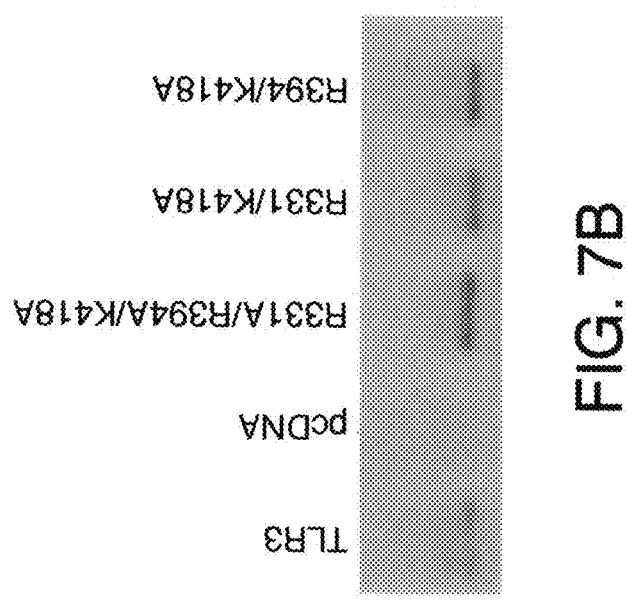

Several residues in the TLR3 ECD were proposed to contact dsRNA. We made alanine mutants of most of the predicted residues as well as the basic residues near the Loop2 of TLR3 ECD. All of the single amino acid changes were largely unaffected in TLR3 activity (FIG. 7A). Combinations of two and three mutations in TLR3 did have some effect, but TLR3 activity remained at more than half of the level for WT. Western blots showed that several of the single and multiple mutants had expression levels and in situ localization similar to that of WT (FIGS. 7B and C). Furthermore, none of the individual residues could be assigned as being critical for TLR3 activity.

Figure 8A:
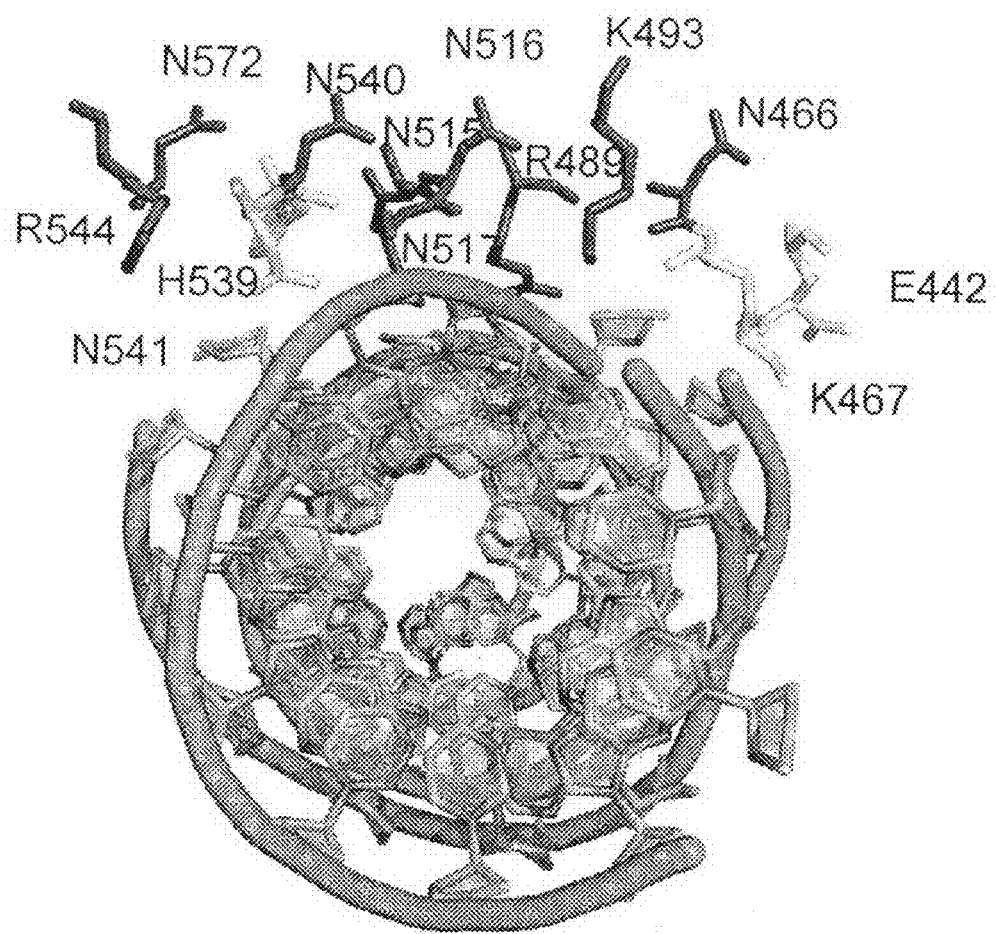
FIG. 8 shows data in examination of the RNA-binding site in TLR3ECD reported by Bell et al. A) A model for poly(I:C) binding to TLR3. The residues that are proposed to be in close contact to poly(I:C) are shown. B) Summary of the effects of amino acid mutations in the charged surface in putative contact with poly(I:C). The plasmids encoding wild-type or mutant TLR3 that were transfected into 293T cells are listed along with their effects on luciferase activity. C) Western blot analysis of some of the mutants tested that had affects on TLR3 activity. The western was probed with the monoclonal antibody, IMG315A.

The RNA-binding surface of TLR3 may be an asparagine-rich surface on the side and C-terminal third of the 3ECD solenoid. Mutations of two residues, H539 and N541, had severe effects on TLR3 activity in cell-based assays. To better visualize the potential contact sites, we used the coordinates of a structure of poly(I:C) (PDB ID code 1QC0) and attempted to dock the molecule into this portion of the TLR3 ECD (FIG. 8A). Residues R544, N540, N516, and N466 are all within the patch that could interact with poly(I:C). Interestingly, when viewed from the end of the poly(I:C) helix, residues E442 and K467 predicted to be involved in TLR3 oligomerization, are at the other side of the RNA molecule and could either contact poly(I:C) and/or be affected by poly (I:C) binding.

Figures 8B, 8C:
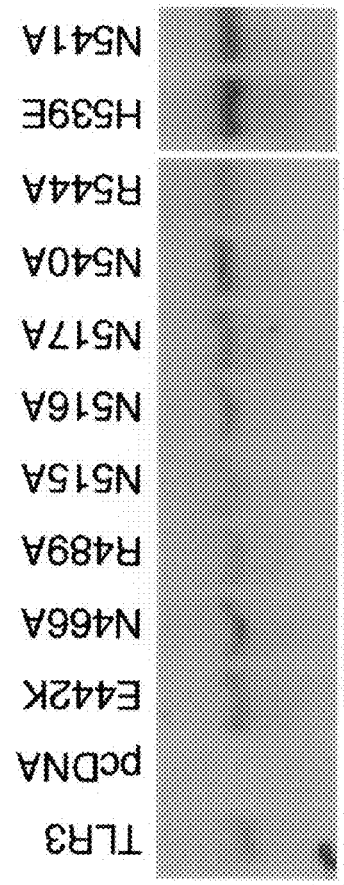

We made mutants H539E and N541A and other mutations in the putative RNA-binding surface. Mutants H539E and N541A had TLR3 activity near background levels (FIG. 8B). Furthermore, adjacent mutations not previously tested by Bell et al., N466A and N540A, also reduced TLR3 activity to background level.

Some changes at the same positions in TLR3 that we tested had different effects than reported, possibly due to the identity of the altered residue. It was reported that N515D and N516L did not affect TLR3 activity. We found that N515A and N516A reduced TLR3 activity to 47 and to 36% of WT. Also, mutant N572A had 55% activity of the WT. Lastly, R489A and N517A reduced TLR3 activity to nearly background while Bell et al., reported that R489A and N517A had more than 50% activity. Western blots of these mutant proteins showed that they are produced in 293T cells, although some, such as N515A, were present in slightly lower amounts compared to WT and could have contributed to decreased TLR3 activity (FIG. 8C). The results demonstrate that charged surface characterized by enriched asparagines in LRR17 to 20 on the side of the solenoid is important for TLR3 function.

Figures 9A, 9B, 9C:
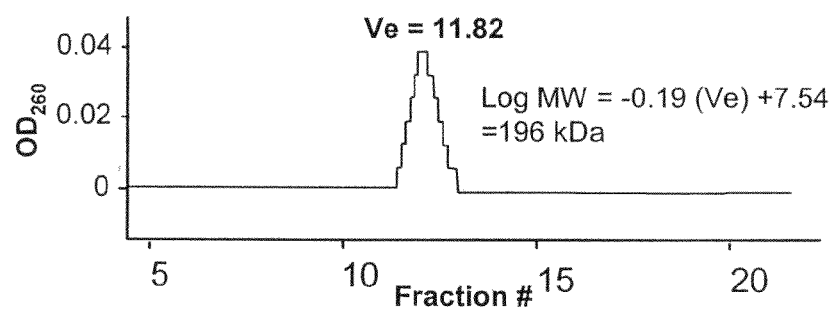
FIG. 9 shows data in examination of residues that may mediate TLR3 oligomerization. A) Dynamic light scattering result of TLR3ECD examined as a function of pH. B) A gel filtration analysis of the elution profile of TLR3ECD. The fractions containing the peak of hTLRECD were detected by SDS-PAGE and staining the protein with silver. C) Effects of mutations in residues participating in TLR3 oligomerization on TLR3 activity. D) Intracellular localization of E442K, which is defective for TLR3 activity.

The putative RNA-binding patch is spatially close to the putative dimerization domain in TLR3 ECD, suggesting a relationship between these two activities. The TLR ECD could exist as a dimer in both 3-D and 2-D crystal lattices. However, that observation might be due to the high protein concentrations needed for crystal formation. Therefore, we examined whether hTLR3ECD could exist in an oligomeric state at lower protein concentrations using dynamic light scattering analysis. The mass of hTLR3ECD monomer is ~100 kD, as determined by mass spectrometry and SDS-PAGE. In a PBS solution, hTLR3ECD (at 25 µg/ml) had a hydrodynamic radius of corresponding to a protein of 178±36 kDa (FIG. 9A). When tested in sodium acetate buffered from pH 6.0 to 4.8, the mass of hTLR3ECD in solution was between 172 kDa to 230 kDa, demonstrating that hTLR3ECD can exist as a dimer in solution in the absence of ligand, and at pHs typically found in an acidic vesicle. We also subjected hTLR3ECD to gel filtration chromatography in comparison to molecular mass markers and it eluted with a peak at 196 kDa, confirming that hTLR3ECD exists predominantly as a dimer (FIG. 9B).

Figure 9D:
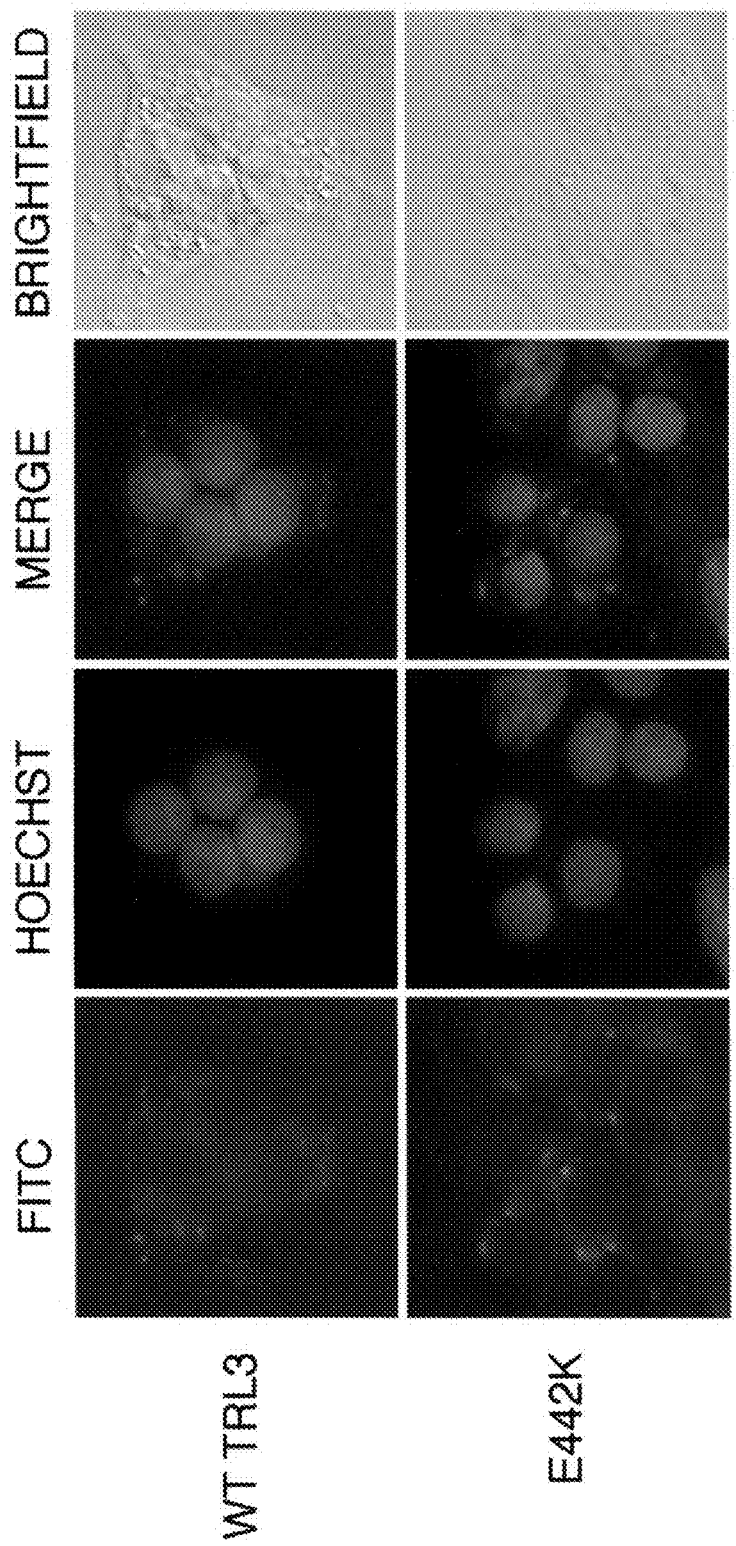

Residues E442 and K467, and also K547 and D575 were predicted to form salt bridges as a part of the interaction between TLR3 subunits. A number of amino acid substitutions were made to test this prediction. Mutant K467A and K467E, only reduced TLR3 activity to 76 and 60% of WT, respectively (FIG. 9C). Mutants E442A, E442D retained more than 62% of the wild-type activity, but changing E442 to a lysine reduced TLR3 activity to 25% of the WT. Localization of E442K in 293T cells showed that it is expressed similar to WT (FIG. 9D). Also, K547A and D575A mutants had negligible effect on activity of the protein as measured by NF-κB activation (FIG. 9C). However, we note that a double mutant E442K/K467E had 66% of the wild-type TLR3 activity. This suggests that the reduction of activity seen with E442K can be partially compensated with the K467E mutation. These results identify that a negatively charged residue at position 442 is important for TLR3 function, but our results do not support the idea that these residues form simple salt bridges since neither E442A nor K467A reduced TLR3 activity significantly. It is possible that that some changes at this position could be better compensated by a network of interactions involving two ECD molecules.

Given the difficulty to assessing the oligomerization state of TLR3 in cells, we used a genetic assay to assess whether mutant versions of TLR3 could suppress the activity of wild-type TLR3, i.e. to act as a dominant negative. The mechanistic basis for the dominant negative activity of a mutant TLR3 is not understood, and even though the inventor does not intend that the claims be limited by any particular mechanism, two likely possibilities exist: 1) a mutant TLR3 is unaffected for binding to the wild-type TLR3, but cannot carry out other activities needed to activate gene expression. Therefore, the mutant protein traps the WT in an inactive state. 2) The mutant protein exists as monomer and retains the ability to titrate ligands and/or accessory factors away from the WT.

Figure 10A:
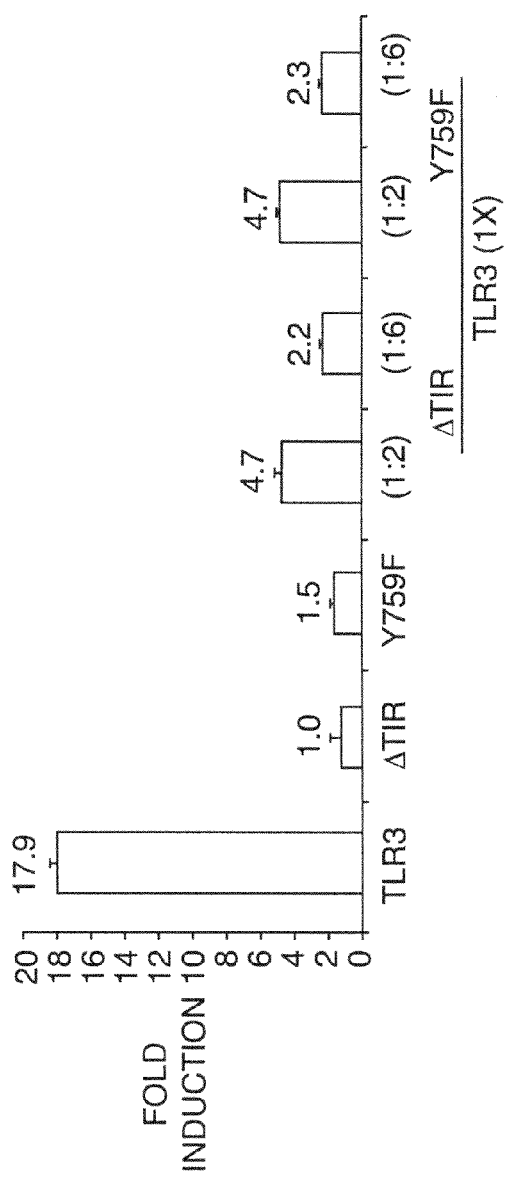
FIG. 10 shows data in assessing the ability of TLR3 variants to act as dominant negatives. A) The ability of mutants ΔTIR and Y75F to activate TLR3 activity and to act as dominant negatives. In all of these assays, 1× denotes that the plasmid is present at 15 ng per transfection. The dominant negative assays were performed with 2× and 6× this concentration. B) A demonstration that increasing poly(I:C) induction could not reverse the dominant negative effect of ΔTIR. C) A summary of the assays for dominant negativity by several mutations that are defective for TLR3 activity. The mutants selected for analysis are also ones that are expressed well, as determined by Western blots. D) A summary of the results from selected mutants built into the context where the TIR domain was deleted (ΔTIR). This construction is useful to confirm the dominant negative result since the mutants cannot activate NF-kB in the absence of the TIR domain, thus reducing the background for the assay.
Figure 10B:
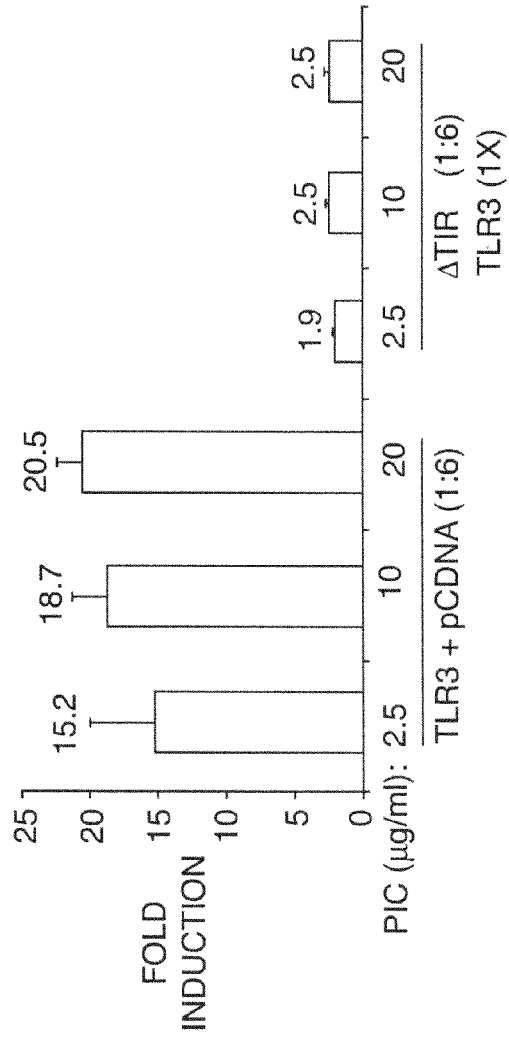

The TLR family proteins consist of an extracellular leucine-rich repeat (LRR), a transmembrane region (TM) and a cytoplasmic tail containing a Toll/IL-1 receptor homology (TIR) domain. To examine the basis for dominant negativity/dimer formation, we used ΔTIR, a known dominant negative version of TLR3 that lacks the TIR domain. See Funami et al., (2004). *Int. Immunol.* 16, 1143-1154. Since ΔTIR is inactive for TLR3 activity, all of the output of the assay is from the co-transfected wild-type TLR3. At 2- or 6-fold molar excess of the wild-type TLR3, ΔTIR suppressed TLR3 activity to 26 and 12%, compared to an assay containing wild-type TLR3 challenged with comparable amounts of the empty vector (FIG. 10A). If the dominant negative effect of ΔTIR occurs by titrating away the ligand poly(I:C), then increasing poly(I:C) concentration should at least partially reverse the dominant negative effect. To test this, a four- or eight-fold higher concentration of poly(I:C) were added to the cells and no significant change in the dominant negative effect of ΔTIR was observed (FIG. 10B), suggesting that dominant negative effect is not due to ΔTIR titrating away the ligand. Similar results were obtained even when ΔTIR was present at 1:1 ratio to that of WT.

If the dominant negative activity were due to protein-protein interaction, then mutations that affect RNA-binding without affecting protein-protein interaction would be dominant negative. We tested mutants H539E and N466A. Both mutants retained their ability to act as dominant negatives, reducing TLR3 activity to 16 and 17% respectively when present at six molar excess of WT, comparable to the effects of ΔTIR (14%) (FIG. 10C).

We also found that mutant Y759F, a mutation that abolishes TIR function was also a dominant negative to similar levels as ΔTIR (FIG. 10A). Together with the results from ΔTIR, two properties are required for TLR3 activity: proper interaction between ECDs and between the TIRs.

The dominant negative assay was used to assess whether various mutations in TLR3 that significantly reduced TLR3 activity can retain protein-protein interaction. Cysteine mutants C37A and C696A were only able to reduce wild-type TLR3 activity to 61 and 76%, respectively, at six molar excess of WT (FIG. 10C). When constructed as a version lacking the TIR domain, C37A and C696A both were poor dominant negatives (FIG. 10D) confirming that the disulfide-forming cysteines are required for proper protein-protein interaction. The disulfides may be contributing to protein-protein interaction indirectly, by affecting the stability of the protein and/or proper localization of TLR3.

Mutant E442K that mapped to be at the right edge of the poly(I:C) binding surface FIG. (8A) and predicted to act in dimerization, was also a poor dominant negative. At six molar excess to the WT, E442K could only reduced wild-type TLR3 activity to 51% (FIG. 10C). ΔTIR version of E442K named E442KΔTIR was also a poor dominant negative (FIG. 10D), supporting the hypothesis that E442 contributes to protein-protein interaction.

Mutant K467E was hypothesized to play a role in 3ECD dimerization. However, since this mutant retained 60% of the TLR3 activity, we tested it for dominant negativity only when it lacked the ΔTIR domain. K467EΔTIR inhibited TLR3 activity to 27% at six fold molar excess, suggesting that mutation K457E did not affect dominant negativity (FIG. 10D).

Another mutant that affected TLR3 activity dramatically was ΔL2. Both ΔL2 and ΔL2ΔTIR were poor dominant negatives (FIG. 10C, 10D). Based on these results, we propose that E442 and Loop2, that are near the poly(I:C) binding surface, are required for interactions between TLR3 subunits.

Mutants N517A, N540A, and N541A had different abilities to inhibit the activity of WT TLR3, ranging from N517A and N541A that were able to partially retain dominantly negative activity to N540 that is a poor dominant negative. These results suggests some of the residues in the asparagine-rich surface of the 3ECD that putatively contacts poly(I:C) can participate in protein-protein interaction to result in a dominant negative phenotype.

We find that the recombinant TLR3ECD protein can be demonstrated to contain at least one disulfide bond that involves C28 and C37, as determined by mass spectrometry analysis. Furthermore, all of the cysteines putatively involved in disulfide bond formation are involved in TLR3 activity. We have also demonstrated that Loop1 within LRR12 of the 3ECD is dispensable for TLR3 activity. In fact, Loop1 may be useful as a place to insert a specific tag to follow TLR3 localization. We also demonstrated that hTLR3ECD can be crosslinked to poly(I:C) in pH conditions similar to that of acidic vesicles and that non-dsRNA are poor competitors for this crosslinking between TLR3 and poly(I:C). Also, TLR3ECD appears to exist as a dimer in solution in the absence of ligand.

There is an overlap in the TLR3 ECD residues that are required for poly(I:C) binding with those required for dominant negativity, the mechanistic basis of which is likely due to the interaction between a nonfunctional protein binding to a wild-type TLR3 through their ECD domains. Using the dominant negative assay, mutations that severely affected TLR3 activation of downstream reporter activity can be separated into those that retain the ability to act as dominant negatives and those that cannot. Interestingly, some, but not all of the putative RNA-binding surface in TLR3 are beneficial for dominant negative effect of TLR3. Also, Loop2 in LRR20 is beneficial for dominant negativity, suggesting a role in protein-protein interaction. Our mutational analysis supports claims for the interactions between 3ECD subunits. Most of the residues, including H539 and N541 that are suggested to bind RNA have a considerable overlap between the activities of RNA binding and dimerization.

Figure 11A:
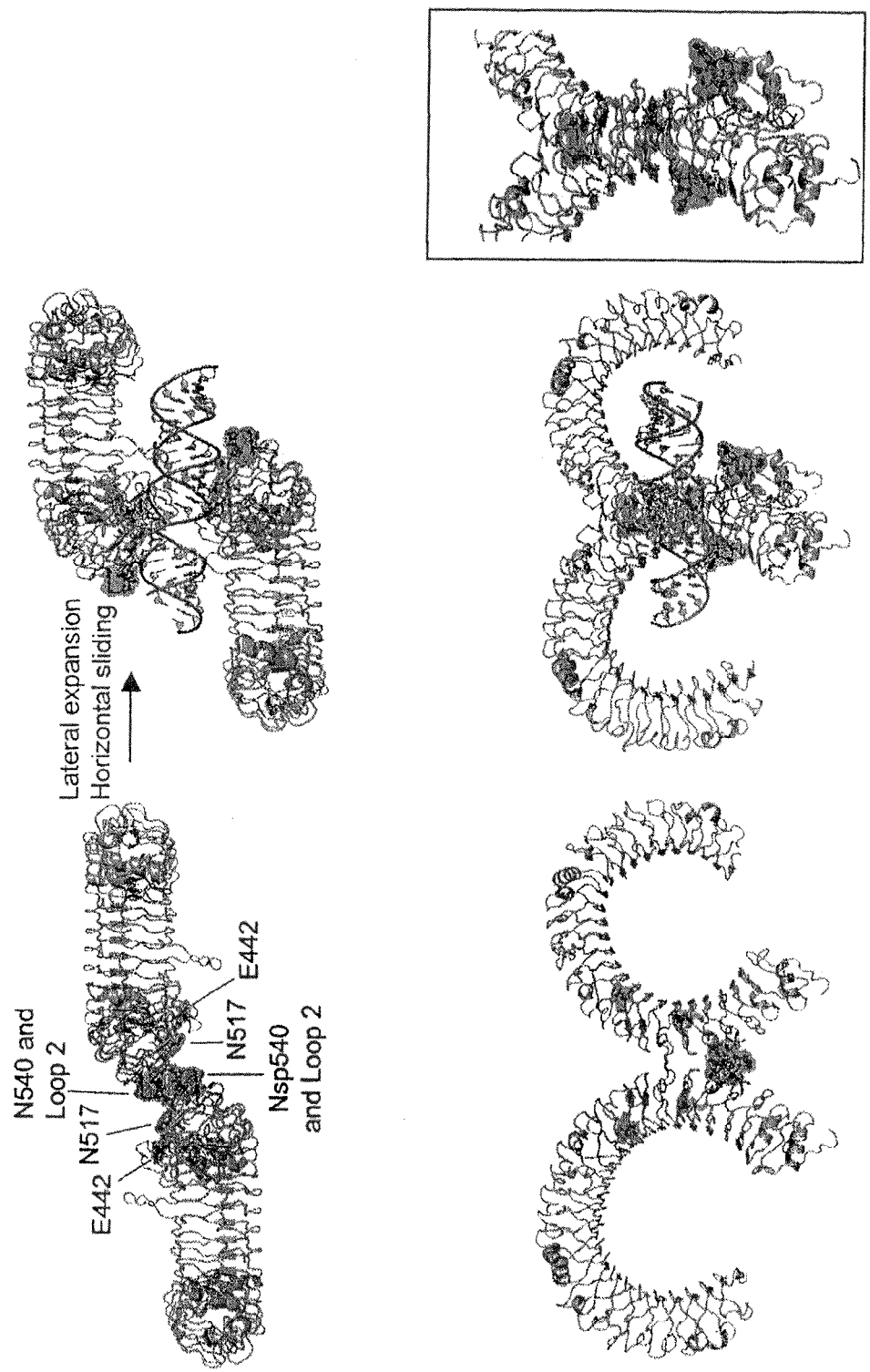
FIG. 11 illustrates a model for the interaction between TLR3ECD subunits and with dsRNA. A) The top and side views of the 3ECD (PDB id 2A0Z) without and with a dsRNA (PDB id 1QC0). The ECD dimer as well as its complex with RNA was obtained through manual docking. The boxed panel highlights the interactions between the C-terminal portions of two ECD molecules in the RNA-bound state. However, the RNA was removed to allow better visualization of the proteins involved in this interaction. B) A cartoon model of full-length TLR3 illustrating how ECD ligand binding can lead to dimerization and subsequent activation of the TIR domain.
Figure 11B:
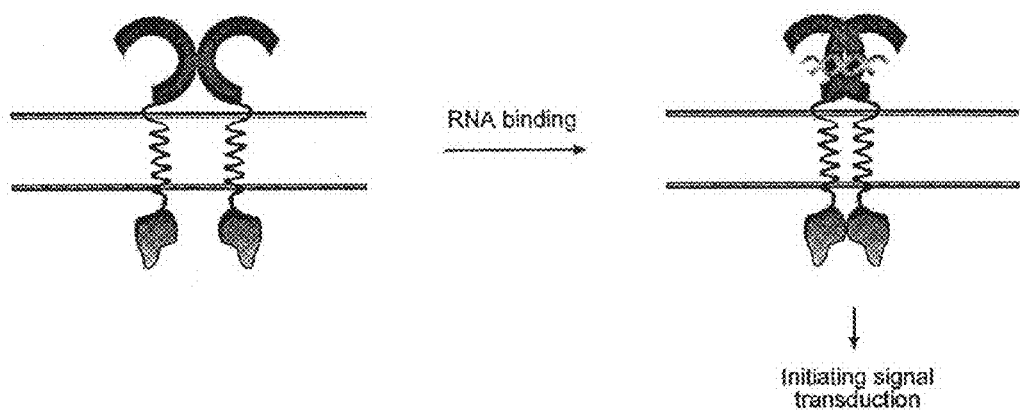
Figure 14:
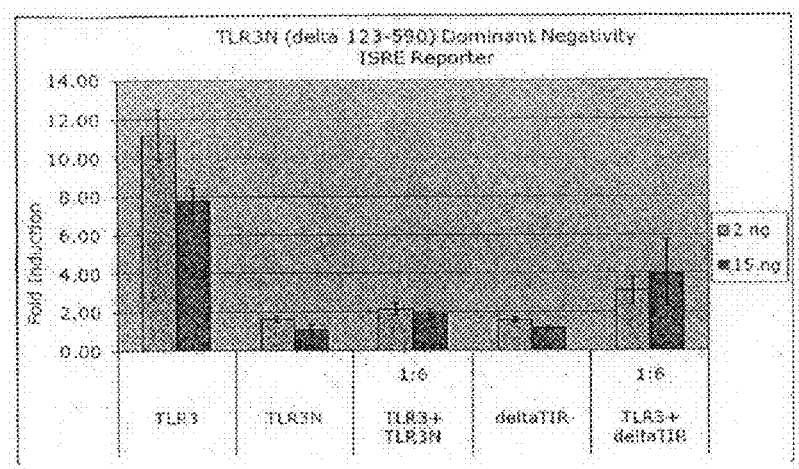
FIG. 14 shows data in assessing the ability of TLR3 variants to act as dominant negatives.
Figure 15:
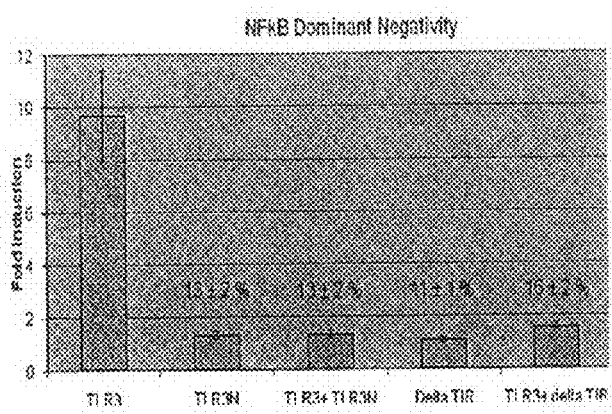
FIG. 15 shows data in assessing the ability of TLR3 variants to act as dominant negatives

We believe that TLR3 can exist in an oligomerized state in the absence of ligand mostly through Loop2 interactions. However, the ligand binding will cause rearrangement in the dimer leading to sliding of the two molecules towards each other laterally while the two molecules are being pushed to accommodate the dsRNA (FIG. 11A). In this ligand bound form, then residues E442 and N517 will interact primarily with the dsRNA to stabilize the complex. The resultant conformational change due to the sliding of the protein subunits may stimulate the interaction of the TIR domains, the subsequent dimerization of which, will lead to the activation of the signal transduction pathway (FIG. 11B).

Pharmaceutical Compositions

The compositions comprising the active compound include bulk-drug compositions useful in the manufacture of pharmaceutical compositions (e.g., impure or non-sterile compositions) and pharmaceutical compositions (i.e., compositions that are suitable for administration to a patient) that can be used in the preparation of unit dosage forms. Such compositions optionally comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of the active compound and another therapeutic or prophylactic agent, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a patient, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylethyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the active compound and optionally another therapeutic or prophylactic agent are formulated in accordance with routine procedures as pharmaceutical compositions adapted for intravenous administration to human beings. Typically, the active compound(s) for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, in tablet or pill form, the compositions can be coated to delay disintegration and absorption in the gastrointestinal tract providing a sustained action over an extended period of time. Selectively permeable membranes surrounding an osmotically active driving compound are also suitable for an orally administered of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound in oily or emulsified vehicles which allow it to disperse only slowly in the serum.

Pharmaceutical compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosal (such as buccal, vaginal, rectal, sublingual) administration. In one embodiment, local or systemic parenteral administration is used.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the pharmaceutical compositions can take the form of tablets or lozenges formulated in conventional manner.

For administration by inhalation, the pharmaceutical compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The pharmaceutical compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The pharmaceutical compositions can also be formulated in rectal compositions such as suppositories or retention enemas, e.g., containing conventional suppository bases such as cocoa butter or other glycerides.

In addition to the formulations described previously, the pharmaceutical compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The invention also provides that a pharmaceutical composition is packaged in a hermetically sealed container such as an ampoule or sachet indicating the quantity. In one embodiment, the pharmaceutical composition is supplied as a dry sterilized lyophilized powder or water free concentrate in a hermetically sealed container and can be reconstituted, e.g., with water or saline to the appropriate concentration for administration to a patient.

In other embodiments of the invention, radiation therapy agents such as radioactive isotopes can be given orally as liquids in capsules or as a drink. Radioactive isotopes can also be formulated for intravenous injection. The skilled oncologist can determine the preferred formulation and route of administration.

The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician'S Desk Reference ($56^{th}$ ed. 2002, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of inflamed tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

In another embodiment, the active compound can be delivered in a vesicle, in particular a liposome.

In yet another embodiment, the active compound can be delivered in a controlled release system. In one embodiment, a pump can be used. In another embodiment, polymeric materials can be used.

The amount of the active compound that is effective in the treatment or prevention of heart conditions can be determined by standard research techniques. For example, the dosage of the active compound which will be effective in the treatment or prevention of heart conditions can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors which will be known to one skilled in the art. Such factors include the disease to be treated or prevented, the symptoms involved, the patient's body mass, the patient's immune status and other factors known by the skilled artisan.

The precise dose to be employed in the formulation will also depend on the route of administration, and the seriousness of the disease-related wasting, and should be decided according to the judgment of the practitioner and each patient's circumstances. Effective doses can be extrapolated from dose-response curves derived from in vitro or animal model test systems.

The dose of the active compound to be administered to a patient, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, patient condition (such as weight), and/or the route of administration.

The general range of effective amounts of the active compound alone or in combination with another prophylactic or therapeutic agent(s) are from about 0.001 mg/day to about 1000 mg/day, more preferably from about 0.001 mg/day to 750 mg/day, more preferably from about 0.001 mg/day to 500 mg/day, more preferably from about 0.001 mg/day to 250 mg/day, more preferably from about 0.001 mg/day to 100 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

EXAMPLES

Example 1

Mutagenesis Analysis

Antisera to TLR3 and poly(I:C), were purchased from Imgenix Inc. (San Diego, Calif.). Dithiothreitol (DTT), iodoacetamide and trypsin were purchased from sigma Chemical Co. The water used in all procedures was purified using a Millipore Milli-Q UV plus purification system. All the organic solvents used for mass spectrometry were HPLC grade and all the other chemicals were reagent grade. The fluorescent dye that stains acidic membrane, Lysotracker, was purchased from Molecular Probes (Eugene Oreg.). The 40 bp poly(I:C) was chemically synthesized. A 20-bp poly(I:C) was made by treating polyinosinic acid and polycytidylic acid with 1M NaOH for 5 minutes, and then separating the bands on a denaturing gel and cutting out the 20-nt bands and annealing them.

To obtain biochemical evidence for disulfide bonds in TLR3, we used mass spectrometry to examine the recombinant TLR3 ECD purified from human cells, named hTLR3ECD. One aliquot of hTLR3ECD was reduced and alkylated similar to protocols in Sechi, S., and Chait, B. T. *Anal. Chem.* 1998, 70, 5150-5158. The other aliquot was diluted with 10 uL of 50 mM ammonium bicarbonate, pH=8. Each aliquots was then thermally denatured at 90° C. for 15 min. The thermally denatured proteins were digested with sequencing grade modified trypsin at 37° C. for overnight. The molar ratio of trypsin to protein used is 1:40. Each sample was desalted using a $C_{18}$Zip Tip (Millipore) before analysis by mass spectrometry (MS) utilizing an ABI 4700 Proteomics Analyzer (Applied Biosystems, Framingham, Mass.). 4-hydroxy-(α-cyanocinnamicacid (5 mg/ml in 50% acetonitrile, 0.1% trifluoroacetic acid) was used as a matrix and mixed 1:1 with the desalted sample and spotted on the MALDI plate. All spectra were taken manually. For the tandem MS experiments the acceleration was set at 1 kV and the collision gas was atmosphere.

The wild-type TLR3 plasmid was previously described in Sun et al. (2006). *J Biol. Chem.* 281, 11144-11151. Site-directed mutations were made using oligonucleotides annealed to the target sequence and the QuickChange kit (Stratagene Inc., San Diego Calif.). Sequences of the oligonucleotides will be made available upon request. Several clones that resulted from the mutational analysis were sequenced to confirm the mutation. Mutant clones with affected activity were sequenced to confirm the presence of the mutation and the absence of unintended changes in the protein.

The model of the TLR3 ectodomain was based on the crystal structure determined by Bell et al. (2005) *Proc Natl Acad Sci USA* 102, 10976-10980. Two TLRECD molecules were docked into a dimer based on Bell et al. (2006). *Proc Natl Acad Sci USA* 103, 8792-8797. (13). The manual docking was performed in the Quanta molecular modeling environment (version 2000, Accelrys). The result was rendered using Pymol (version 0.99, DeLano Scientific LLC).

Cells were plated on LabTek II CC2 treated chamber slides (Nunc Intl., Naperville, Ill.) and transfected with plasmids in Lipofectamine2000 (Invitrogen, Carlsbad, Calif.). Each TLR3 mutant was visualized 24 hours post transfection with a Zeiss Axioplan fluorescent microscope via immunofluorescence. Briefly, the cells were removed from the incubator and rinsed with PBS before being fixed with 4% formaldehyde in PBS and permeabilized with 0.1% Triton X-100. The cells were then incubated at room temperature in the dark for at least 1 hour in anti-TLR3 FITC-conjugated monoclonal antibody (Imgenex315A San Diego, Calif.). The cells were washed and counterstained with Hoechst 33342 dye (Molecular Probes, Eugene, Oreg.) before being mounted in a buffered glycerol aqueous mounting medium.

293T cells were transiently transfected with wild type TLR3, mutant TLR3 or control pcDNA as described above. Thirty-six hours post transfection, the cells were lysed using passive lysis buffer (Promega Inc.) and sonicated to degrade chromosomal DNA. Equal amounts of proteins from each sample were separated on NuPAGE 4-12% bis-tris gel (Invitrogen), blotted onto PVDF membrane and probed with anti-TLR3 MAb IMG315A (Imgenex Inc.). The blots were developed with peroxidase conjugated secondary antibodies and ECL-plus western blotting detection system (Amersham Biosciences).

FACS analyses were performed with 293T cells grown in 6-well collagen-coated plates (BD Biosciences) at a concentration of $2 \times 10^6$ cells/well. The cells were transfected with 1 μg of the appropriate plasmids using Lipofectamine 2000 (Invitrogen Inc.). Eighteen to twenty-four hours after transfection, the cells were harvested and washed twice with ice-cold FACS buffer (1×PBS (10 mM Phosphate, 150 mM NaCl, pH7.4; +3% fetal bovine serum+0.04% sodium azide) before suspension at ~$2 \times 10^7$ cells/mL in FACS buffer. The cells were stained for 30 minutes at 4° C. with 1 μg PE-labeled anti-human TLR3 mAb (TLR3.7, purchased from eBioscience, San Diego, Calif.) or a negative control mouse IgG1 control antibody. The antibodies were added to cells grown in 96 well plates and incubated for 30 min on ice in the dark. The cells were washed twice with FACS buffer to remove unbound antibody, then resuspended in FACS buffer. Viaprobe (BD Biosciences) was used to exclude dead cells. The cells were transferred to the appropriate tubes and analyzed using a FACS Calibur machine (BD Biosciences).

Example 2

Regulating TLR3 can modulate the inflammatory response that can prove deadly or debilitating in sepsis, arthritis, and asthma, to name only a few diseases. TLR3 needs to form homo-oligomers as part of the mechanism of action (MOA). This MOA suggests that mutant versions of TLR3 that can suppress signaling of the wild-type TLR3 (so called dominant negative mutants) can be used to modulate the inflammation response. Dominant negative TLR3 have been reported, including TLR3-DeltaTIR, which lacks the intracellular signaling domain of TLR3, indicating that the extracellular domain is required for dominant negativity (Ranjith-Kumar et al., 2007. J. B. C. 282, p. 7668). Other dominant negatives include mutations in the extracellular domain of TLR3 (ibid).

Surprisingly, we have identified a TLR3 mutant that lacks a substantial portion of the extracellular domain. Mutant TLR3N lacks residues 123-590 (deleting the motifs from LLR4 to part of LLR 22) (SEQ ID NO:48). Missing in TLR3N are Loop 2 and several of the previously identified residues demonstrated to be required for TLR3 dimerization (ibid). Analysis of TLR3N thus uncovered a second pathway for dominant negative inhibition of TLR3 signaling.

We expect that TLR3N can be targeted to the plasma membrane since it contains both the signal peptide as well as the N-terminus and C-terminus caps of TLR3 (Bell, J. K. et al., (2005) Proc. Natl. Acad. Sci. U.S.A. 102, 10976.

Dominant negativity assays have been conducted for TLR3N using reporter luciferase driven from either the NF-KB or the ISRE promoters. Renilla luciferase was used as a transfection control and all data is normalized as folds over the Renella control. The results are in agreement. In addition, TLR3N was compared with TLR3deltaTIR and its dominant negative activity was found to be comparable to that of TLR3delta-TIR.

TLR3 is an important regulator of the inflammation response. The discovery of a new dominant negative mutant TLR3 with a different MOA than previous mutants can form the basis of a new class of regulators of the inflammation response.

The invention claimed is:

1. A composition comprising a Toll-like receptor (TLR)3 mutant polypeptide, wherein said polypeptide is a dominant negative inhibitor of a TLR protein, wherein said TLR3 mutant polypeptide comprises a mutation in Loop2.

2. The composition of claim 1, further comprising a pharmaceutical carrier.

3. A composition comprising a Toll-like receptor (TLR)3 mutant polypeptide, wherein said polypeptide is a dominant negative inhibitor of a TLR protein, wherein said mutant comprises the sequence set forth in SEQ ID NO:1 is with one or more amino acid substitutions selected from the group consisting of C242A, C356A, C28A, C37A, C37S, C37M, C95A, C122A, C122S, C122M, C649A, C649S, C649M, C651A, C696A, C696S, C696M, R65A, K89A, K117A, K137A, K139A, K147A, K163A, K210A, R331A, R394A, K418A, K493A, K589A, K613A, K627A, R635A, R643A, H539E, N541A, N466A, R489A, N515A, N516A, N517A, N540A, R544A, N572A, E442A, E442D, E442K, K467A, K467E, K547A, and D575A.

4. A composition comprising a TLR3 mutant polypeptide, wherein said polypeptide is a dominant negative inhibitor of a TLR protein, wherein said polypeptide comprises the motif HANPGGIY (SEQ ID NO:41).

5. A composition comprising a polypeptide mutant of SEQ ID NO: 1, wherein said mutant has a single amino acid substitution selected from the group consisting of C242A, C356A, C28A, C37A, C37S, C37M, C95A, C122A, C122S, C122M, C649A, C649S, C649M, C651A, C696A, C696S, C696M, R65A, K89A, K117A, K137A, K139A, K147A, K163A, K210A, R331A, R394A, K418A, K493A, K589A, K613A, K627A, R635A, R643A, H539E, N541A, N466A, R489A, N515A, N516A, N517A, N540A, R544A, N572A, E442A, E442D, E442K, K467A, K467E, K547A, and D575A.

* * * * *